US011957745B2

(12) United States Patent
Crowe, Jr.

(10) Patent No.: US 11,957,745 B2
(45) Date of Patent: Apr. 16, 2024

(54) HUMAN JAPANESE ENCEPHALITIS VIRUS ANTIBODIES AND METHODS OF USE THEREFOR

(71) Applicant: Vanderbilt University, Nashville, TN (US)

(72) Inventor: James E. Crowe, Jr., Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 826 days.

(21) Appl. No.: 16/971,761

(22) PCT Filed: Feb. 22, 2019

(86) PCT No.: PCT/US2019/019118
§ 371 (c)(1),
(2) Date: Aug. 21, 2020

(87) PCT Pub. No.: WO2019/165184
PCT Pub. Date: Aug. 29, 2019

(65) Prior Publication Data
US 2020/0390879 A1    Dec. 17, 2020

Related U.S. Application Data

(60) Provisional application No. 62/633,741, filed on Feb. 22, 2018.

(51) Int. Cl.
*A61K 39/12* (2006.01)
*C07K 16/10* (2006.01)
*G01N 33/569* (2006.01)

(52) U.S. Cl.
CPC .......... *A61K 39/12* (2013.01); *C07K 16/1081* (2013.01); *G01N 33/56983* (2013.01)

(58) Field of Classification Search
None
See application file for complete search history.

(56) References Cited

U.S. PATENT DOCUMENTS

| 2010/0166768 | A1 |   | 7/2010 | Sleeman et al. |
| 2016/0137722 | A1 | * | 5/2016 | Goncalvez ............. C07K 16/10 435/5 |
| 2017/0274063 | A1 |   | 9/2017 | Carra et al. |

FOREIGN PATENT DOCUMENTS

| CN |  | 101226196 A | * | 7/2008 |  |
| WO |  | WO-2009126898 A2 | * | 10/2009 | ......... A61K 47/4853 |
| WO |  | WO 2011/085103 |  | 7/2011 |  |
| WO |  | WO 2011/100620 |  | 8/2011 |  |

OTHER PUBLICATIONS

Fernandez, et al. Mouse and Human Monoclonal Antibodies Protect against Infection by Multiple Genotypes of Japanese Encephalitis Virus. mBio. Feb. 27, 2018;9(1):e00008-18. doi: 10.1128/mBio.00008-18. PMID: 29487230; PMCID: PMC5829823. (Year: 2018).*
Austin et al., "Structural basis of differential neutralization of DENV-1 genotypes by an antibody that recognizes a cryptic epitope" *PLoS Pathog* 8, 2012.
Beltramello et al., "The human immune response to Dengue virus is dominated by highly cross-reactive antibodies antibodies endowed with neutralizing and enhancing activity" *Cell Host Microbe* 8, 271-283, 2010.
Goncalves et al., "Humanized monoclonal antibodies derived from chimpanzee Fabs protect against Japanese encephalitis virus in vitro and in vivo" *J Virol.*, 82:7009-7021, 2008.
Goo et al., "A single mutation in the envelope protein modulates flavivirus antigenicity, stability, and pathogenesis," *PLoS Pathog*, 13(2), 2017.
International Search Report and Written Opinion issued in corresponding PCT Application No. PCT/US2019/019118, dated Jun. 25, 2019.
Jarmer et al., "Variation of the specificity of the human antibody responses after tick-borne encephalitis virus infection and vaccination," *J Virol*, 88:13845-13857, 2014.
Kimura-Kuroda and Yasui, "Antigenic comparison of envelope protein E between Japanese encephalitis virus and some other flaviviruses using monoclonal antibodies," *J Gen Virol*, 67:2663-2672, 1986.
Kimura-Kuroda and Yasui, "Topographical analysis of antigenic determinants on envelope glycoprotein V3 (E) of Japanese encephalitis virus, using monoclonal antibodies." *J Virol*, 45:124-132, 1983.
Kimura-Kuroda and Yasui, "Protection of mice against Japanese encephalitis virus by passive administration with monoclonal antibodies." *J Immunol* 141:3606-10, 1988.
Lin et al., "A functional epitope determinant on domain III of the Japanese encephalitis virus envelope protein interacted with neutralizing-antibody combining sites." *J Virol*, 77:2600-6, 2003.
Luca et al., "Crystal structure of the Japanese encephalitis virus envelope protein." *J Virol*, 86:2337-2346, 2012.
Mason et al., "Molecular characterization of a neutralizing domain of the Japanese encephalitis virus structural glycoprotein." *J Gen Virol*, 70:2037-2049, 1989.
Oliphant et al., "Antibody recognition and neutralization determinants on domains I and II of West Nile virus envelope protein." *J Virol*, 80:12149-12159, 2006.
Robbiani et al., "Recurrent Potent Human Neutralizing Antibodies to Zika Virus in Brazil and Mexico." *Cell*, 169:597-609.e11, 2017.
Shrestha et al., "The development of therapeutic antibodies that neutralize homologous and heterologous genotypes of dengue virus type 1," *PLoS Pathog* 6:e1000823, 2010.
Shimoda et al., "Production and characterization of monoclonal antibodies to Japanese encephalitis virus," *Journal of Veterinary Medicine*, 75(8):1077-80, 2013.
Smith et al., "The potent and broadly neutralizing human dengue virus-specific monoclonal antibody 1C19 reveals a unique cross-reactive epitope on the bc loop of domain II of the envelope protein." *MBio* 4:e00873-13-e00873-13, 2013.

(Continued)

*Primary Examiner* — Benjamin P Blumel
*Assistant Examiner* — Jeffrey Mark Sifford
(74) *Attorney, Agent, or Firm* — Parker Highlander PLLC

(57) ABSTRACT

The present disclosure is directed to antibodies binding to and neutralizing Japanese Encephalitis virus and methods for use thereof.

20 Claims, 14 Drawing Sheets

Specification includes a Sequence Listing.

(56) References Cited

OTHER PUBLICATIONS

Stiasny et al., "Probing the flavivirus membrane fusion mechanism by using monoclonal antibodies." *J Virol* 81:11526-11531, 2007.
Sukupolvi-Petty et al., "Type- and subcomplex-specific neutralizing antibodies against domain III of dengue virus type 2 envelope protein recognize adjacent epitopes," *J Virol* 81:12816-26, 2007.
Throsby et al., "Isolation and characterization of human monoclonal antibodies from individuals infected with West Nile Virus." *J Virol* 80:6982-92, 2006.
Vratskikh et al., "Dissection of antibody specificities induced by yellow fever vaccination." *PLoS Pathog* 9, 2013.
Wahala et al., "Dengue virus neutralization by human immune sera: Role of envelope protein domain III-reactive antibody" *Virology.* 392(1):103-113, 2009.
Zhang et al. "Passive protection of mice, goats, and monkeys against Japanese encephalitis with monoclonal antibodies." *J Med Virol* 29:133-138, 1989.

\* cited by examiner

|              | 297 300              | 310              | 320              | 330              |
|--------------|----------------------|------------------|------------------|------------------|
| JEV-106      | KGTTYGMCTEKFSFAKNPVDTGHGTVVIELSYSGSDGPCKI |
| JEV-128      | KGTTYGMCTEKFSFAKNPVDTGHGTVVIELSYSGSDGPCKI |
| JEV-143      | KGTTYGMCTEKFSFAKNPVDTGHGTVVIELSYSGSDGPCKI |
| JEV-31       | KGTTYGMCTEKFSFAKNPVDTGHGTVVIELSYSGSDGPCKI |
| JEV-131      | KGTTYGMCTEKFSFAKNPVDTGHGTVVIELSYSGSDGPCKI |
| JEV-117      | KGTTYGMCTEKFSFAKNPVDTGHGTVVIELSYSGSDGPCKI |
| hJEV-69      | KGTTYGMCTEKFSFAKNPVDTGHGTVVIELSYSGSDGPCKI |
| hJEV-75      | KGTTYGMCTEKFSFAKNPVDTGHGTVVIELSYSGSDGPCKI |
| Zika-2,48,67 | KGVSYSLCTAAFTFTKIPAETLHGTVTVEVQYAGTDGPCKV |
| WNV-E16      | KGTTVGVCSKAFKFLGTPADTGHGTVVLELQYTGTDGPCKV |
| DV1-E106     | KGMSYVMCTGSFKLEKEVAETQHGTVLVQVKYEGTDAPCKI |
| DV1-E111     | KGMSYVMCTGSFKLEKEVAETQHGTVLVQVKYEGTDAPCKI |
| DV2-1A1D2    | KGMSYSMCTGKFKVVKEIAETQHGTIVIRVQYEGDGSPCKI |
| DV3-2H12     | KGMSYAMCLNTFVLKKEVSEIQHGTILKYEYKGEDAPCKI |
| DV4-4E11     | KGMSYTMCSGKFSIDKEMAETQHGTTVVKVKYEGAGAPCKV |

*FIG. 3A (Cont'd)* hJEV-69 hJEV-75

JEV-169

FIG. 3C

HUMAN JAPANESE ENCEPHALITIS VIRUS ANTIBODIES AND METHODS OF USE THEREFOR

PRIORITY CLAIM

This application is a national phase application under 35 U.S.C. § 371 of International Application No. PCT/US2019/019118, filed Feb. 22, 2019, which claims benefit of priority to U.S. Provisional Application Ser. No. 62/633,741, filed Feb. 22, 2018, the entire contents of each of which are hereby incorporated by reference.

FEDERAL FUNDING

This invention was made with government support under HHSN272201400018C awarded by the National Institutes of Allergy and Infectious Disease/National Institutes of Health. The government has certain rights in the invention.

BACKGROUND

1. Field of the Disclosure

The present disclosure relates generally to the fields of medicine, infectious disease, and immunology. More particular, the disclosure relates to human antibodies binding to Japanese Encephalitis Virus (JEV).

2. Background

Flaviviruses are a group of arthropod-borne, enveloped, positive-stranded RNA viruses that include pathogens of global health significance such as WNV, dengue virus (DENV), yellow fever virus (YFV), and Zika virus (ZIKV). For some flaviviruses, including YFV, Japanese encephalitis virus (JEV), tick-borne encephalitis virus (TBEV), and DENV, licensed vaccines are available. The development of neutralizing antibodies (NAbs) in vitro is a correlate of protection for most, but not all of these vaccines.

Despite the existence of inactivated and live-attenuated vaccine platforms, Japanese encephalitis virus (JEV) remains a primary cause of viral encephalitis. It is particularly prevalent in Asia with approximately 68,000 clinical cases (Campbell 2011 and WHO|Japanese encephalitis. WHO, 2017) and an estimated 10,000-15,000 deaths per year (Campbell 2011). JEV circulates endemically in southern tropical and sub-tropical areas (e.g., Australia, Indonesia, and Singapore), with epidemics occurring in northern temperate regions (e.g., Japan, Bhutan, and Nepal) (Vaughn et al., 1992 and Liang and Huanyu, 2015). JEV is transmitted primarily by the *Culex tritaeniorhynchus* mosquito and is maintained in an enzootic cycle with pigs and wading birds. In contrast, humans are infected as incidental dead-end hosts (Burke et al., 1985 and Hammon and Tigertt, 1949). The high incidence of JEV in rural areas has been attributed to the presence of open water sources, the preferred breeding grounds for *Culex* mosquitoes (Health, 2015).

Approximately 5 to 15 days after mosquito inoculation of JEV, a non-specific febrile illness develops, characterized by malaise, headache, and general discomfort (WHO|Japanese encephalitis. WHO, 2017). Symptomatic JEV infection is observed most commonly in children in endemic areas, children and adults in epidemic areas, and travelers to endemic and epidemic areas (Vaughn et al., 1992 and Borah et al., 2011). Severe clinical JEV disease occurs in about 1% of infected humans, with progression to encephalitis, seizures, or neurological deficits (Halstead and Solomon, 2010 and Solomon, 2000). Beyond death, which occurs in 20-30% of clinical cases, severe long-term complications include paralysis, dystonia, and cognitive deficits (Solomon, 2000, Solomon et al., 1998 and Chen et al., 2009).

JEV is a flavivirus of the Flaviviridae family and is related to other viruses that cause human disease including Zika (ZIKV), West Nile (WNV), dengue (DENV), tick-borne encephalitis (TBEV), and yellow fever (YFV) viruses. JEV is a ~50 nm enveloped, positive-stranded RNA virus with an ~11-kb genome flanked by 5' and 3' untranslated regions. The genome encodes a single open reading frame that is co- and post-translationally cleaved by viral and host proteases into three structural (capsid (C), pre-membrane (prM), and envelope (E)) and seven non-structural proteins. The E protein is necessary for virus binding, entry, and fusion in host cells (Roehrig et al., 1990), and is divided into three domains: domain I (E-DI) is the central β-barrel domain, domain II (E-DII) is an extended dimerization domain with a distal hydrophobic fusion loop, and domain III (E-DIII) is an immunoglobulin-like fold (Rey et al., 1995). Structural analysis of the JEV E protein shows a smaller dimer interface with increased contacts at the E-DI-DIII pocket, compared to those of related flaviviruses (Luca et al., 2012).

Although most phylogenetic analyses define four JEV genotypes based on sequence variation of the E protein, multiple strains belonging to a fifth genotype were recently identified in Malaysia and South Korea (Mohammed et al., 2011, Uchil and Satchidanandam, 2001 and Takhampunya et al. 2011). The genotypes cluster within particular geographic distributions; for example, GI and GIII strains are more common in temperate regions, whereas GII and GIV are more common in tropical climates (Chen et al., 1990, Chen et al., 1992 and Schuh et al., 2013). GIII has been the predominant genotype historically and as such, existing vaccines against JEV are derived from prototypical GIII strains such as JEV-Nakayama and JEV-SA-14 (Schuh et al., 2013). Recent reports have noted a substantial increase in GI infections in Asian countries, including China and Japan (Wang et al., 2007 and Ma et al., 2003).

The humoral response to JEV, like that of other flaviviruses, is considered necessary for limiting infection, and neutralizing antibody titers often serve as a correlate of protection (Plotkin, 2010). Indeed, JEV type-specific mouse monoclonal antibodies (mAbs) with protective activity (e.g., E3.3) have been identified and were derived against GIII strains (Kimura-Kuroda and Yasui, 1986, Kimura-Kuroda and Yasui, 1988, Mason et al., 1989 and Lin et al., 2003). Moreover, a humanized mAb (B2) that was derived from a chimpanzee immunized with JE-VAX® also protected mice against JEV-Nakayama, a strain of the homologous JEV genotype (GIII) (Goncalvez et al., 2008). Other neutralizing mAbs (e.g., 2H4 and 2F2) protected in goat and monkey models of infection (Zhang et al., 1989) against JEV strains of the homologous genotype to which they were raised.

Notwithstanding these data, no study has comprehensively profiled the inhibitory activity of anti-JEV mAbs against multiple genotypes in vitro and in vivo, and no fully human anti-JEV mAbs have been described. The shift in prevalence from GIII to GI may require a different antibody repertoire for protection against infection and thus has implications for the efficacy of existing vaccines that were derived against GIII.

SUMMARY

Thus, in accordance with the present disclosure, a method of detecting a Japanese Encephalitis virus infection in a subject comprising (a) contacting a sample from said subject with an antibody or antibody fragment having clone-paired heavy and light chain CDR sequences from Tables 3 and 4, respectively; and (b) detecting Japanese Encephalitis virus in said sample by binding of said antibody or antibody fragment to a Japanese Encephalitis virus antigen in said sample. The sample may be a body fluid, such as blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or Western blot. The method may further comprise performing steps (a) and (b) a second time and determining a change in Japanese Encephalitis virus antigen levels as compared to the first assay.

The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant ScFv (single chain fragment variable) antibody, Fab fragment, F(ab')$_2$ fragment, or Fv fragment.

In another embodiment, there is provided a method of treating a subject infected with Japanese Encephalitis virus, or reducing the likelihood of infection of a subject at risk of contracting Japanese Encephalitis virus, comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant ScFv (single chain fragment variable) antibody, Fab fragment, F(ab')$_2$ fragment, or Fv fragment.

The antibody may be an IgG, a recombinant IgG antibody or antibody fragment comprising an Fc portion mutated to alter (eliminate or enhance) FcR interactions, such as a LALA, N297, GASD/ALIE, a glycan modified antibody with altered (eliminated or enhanced) FcR interactions, such as enzymatic or chemical addition or removal of glycans, a genetically modified glycosylating pattern, or an antibody or antibody fragment comprising an Fc portion mutated to enhance FcRn interactions to increase the in vivo half-life and the in vivo protective effect, such as a YTE or LS mutation. The antibody may be a chimeric antibody or a bispecific antibody.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment, such as a VEE replicon, such as gene delivery by injection with a needle, use of an electroporation device, or other physical method.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant ScFv (single chain fragment variable) antibody, Fab fragment, F(ab')$_2$ fragment, or Fv fragment. The antibody may be a chimeric antibod, or is bispecific antibody.

The antibody may be an IgG, a recombinant IgG antibody or antibody fragment comprising an Fc portion mutated to alter (eliminate or enhance) FcR interactions, such as a LALA, N297, GASD/ALIE, a glycan modified antibody with altered (eliminated or enhanced) FcR interactions, such as enzymatic or chemical addition or removal of glycans, a genetically modified glycosylating pattern, or an antibody or antibody fragment comprising an Fc portion mutated to enhance FcRn interactions to increase the in vivo half-life and the in vivo protective effect, such as a YTE or LS mutation. The antibody or antibody fragment may further comprises a cell penetrating peptide and/or is an intrabody.

Also provided is a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant ScFv (single chain fragment variable) antibody, Fab fragment, F(ab')$_2$ fragment, or Fv fragment. The antibody may be a chimeric antibody or a bispecific antibody.

The antibody may be an IgG, a recombinant IgG antibody or antibody fragment comprising an Fc portion mutated to alter (eliminate or enhance) FcR interactions, such as a LALA, N297, GASD/ALIE, a glycan modified antibody with altered (eliminated or enhanced) FcR interactions, such as enzymatic or chemical addition or removal of glycans, a genetically modified glycosylating pattern, or an antibody or antibody fragment comprising an Fc portion mutated to enhance FcRn interactions to increase the in vivo half-life and the in vivo protective effect, such as a YTE or LS mutation. The antibody may be a chimeric antibody or a bispecific antibody. The antibody or antibody fragment may further comprise a cell penetrating peptide and/or is an intrabody.

In a further embodiment, there is provided a vaccine formulation comprising one or more antibodies or antibody fragments characterized by clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant ScFv (single chain fragment variable) antibody, Fab fragment, F(ab')$_2$ fragment, or Fv fragment. The antibody may be a chimeric antibody or a bispecific antibody.

The antibody may be an IgG, a recombinant IgG antibody or antibody fragment comprising an Fc portion mutated to alter (eliminate or enhance) FcR interactions, such as a LALA, N297, GASD/ALIE, a glycan modified antibody with altered (eliminated or enhanced) FcR interactions, such as enzymatic or chemical addition or removal of glycans, a genetically modified glycosylating pattern, or an antibody or antibody fragment comprising an Fc portion mutated to enhance FcRn interactions to increase the in vivo half-life and the in vivo protective effect, such as a YTE or LS mutation. The antibody may be a chimeric antibody or a bispecific antibody. The antibody or antibody fragment may further comprise a cell penetrating peptide and/or is an intrabody.

Furthermore, there is provided a method of determining the antigenic integrity of an antigen comprising (a) contacting a sample comprising said antigen with a first antibody or antibody fragment having clone-paired heavy and light chain CDR sequences from Tables 3 and 4, respectively; and (b) determining antigenic integrity of said antigen by detectable binding of said antibody or antibody fragment to said antigen. The sample may comprise recombinantly produced antigen. The sample may comprise a vaccine formulation or vaccine production batch. Detection comprises ELISA, RIA, western blot, a biosensor using surface plasmon resonance or biolayer interferometry, or flow cytometric staining.

The first antibody or antibody fragment may be encoded by clone-paired variable sequences as set forth in Table 1. The first antibody or antibody fragment may encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The first antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The first antibody fragment may be a recombinant ScFv (single chain fragment variable) antibody, Fab fragment, F(ab')$_2$ fragment, or Fv fragment.

The method may further comprise performing steps (a) and (b) a second time to determine the antigenic stability of the antigen over time. The method may further comprise (c) contacting a sample comprising said antigen with an antibody or antibody fragment having clone-paired heavy and light chain CDR sequences from Tables 3 and 4, respectively; and (d) determining antigenic integrity of said antigen by detectable binding of said antibody or antibody fragment to said antigen. The second antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant ScFv (single chain fragment variable) antibody, Fab fragment, F(ab')$_2$ fragment, or Fv fragment. The method may further comprise performing steps (c) and (d) a second time to determine the antigenic stability of the antigen over time.

Also provided is a neutralizing human monoclonal antibody that binds to Japanese Encephalitis virus (JEV) epitope E-DIII.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

FIGS. 1A-C. Neutralization activity of anti-JEV mAbs. (FIGS. 1A-B) Serum samples from humans previously immunized against JEV with an inactivated virion vaccine were tested against a panel of JEV strains (2372/79 (GI), MAR 859 (GI), Bennett (GII), SA-14 (GIII), SA-14-14-2 (GIII), Nakayama (GIII), and JKT 7887 (GIV)) by focus-forming assay (FFA) for neutralization activity. Serial serum dilutions were incubated with $10^2$ FFU 1 h at 37° C. and Vero cells were subsequently infected and stained. (FIG. 1C) Neutralization curves of human-derived anti-JEV mAbs (hJEV-11, hJEV-69, hJEV-75, and hJEV-80) against the indicated strains. All data is representative of three independent experiments performed in triplicate.

FIGS. 2A-B. Mechanism of neutralization by anti-JEV mAbs. (FIG. 2A) The pre-attachment inhibition assay (solid lines) was performed by incubating $10^2$ FFU of JEV-SA-14-14-2 with serial dilutions of mAbs starting at 10 µg/ml for 1 h at 4° C. before adding to pre-chilled Vero cells at 4° C. and subsequently following the FFA protocol. The post-attachment assay (dashed lines) was performed by adding $10^2$ FFU of JEV-SA-14-14-2 to cells for 1 h at 4° C. After extensive washing to remove unbound virus, serial dilutions of mAbs were added starting at 10 µg/ml and incubated for 1 h at 4° C., and the FFA assay then was completed at 37° C. Data is representative of three experiments performed in triplicates. (FIG. 2B) Fusion from without assay (FFWO) was performed after incubating Vero cells at 4° C. with JEV-SA-14 (MOI of 50) for 2 h. For these experiments, JEV-SA-14 was used instead of JEV-SA-14-14-2 because it could be grown to higher titer. Cells were washed extensively and the indicated mAbs were added for 30 min. Plasma membrane fusion was induced by exposing the cells briefly (~7 min) to an acidic pH buffer. After pH normalization, cells were incubated with 10 nM concanamycin for 24 hours to inhibit infection via the endosomal pathway and collected, fixed, permeabilized, and stained for E protein expression. The treatment and percentage of positive cells are shown FIGS. 3A-C Structural representation of JEV E epitopes defined by alanine scanning mutagenesis and HDX.

(FIG. 4A) Four to five week-old male C57BL/6 mice were passively administered 10 µg of indicated human mAbs via intraperitoneal injection one day prior to inoculation with $10^2$ FFU of JEV-Nakayama via the subcutaneous route. (FIGS. 4B-C) 250 µg of indicated mAb were administered 5 days post-infection to (FIG. 4B) four to five week-old mice infected with $10^2$ FFU of JEV-Nakayama hJEV-75, n=8) or ((FIG. 4C) 3-week old mice infected with 10' FFU of JEV-2372/79 (hJEV-75, n=9). Data is pooled from at least two independent experiments. Survival was analyzed for each mAb compared to isotype-control mAb by the log-rank test (*P<0.05, P<0.01, *P<0.001, ****P<0.0001, and ns indicates no significance).

DESCRIPTION OF ILLUSTRATIVE EMBODIMENTS

Figures 1A, 1B:
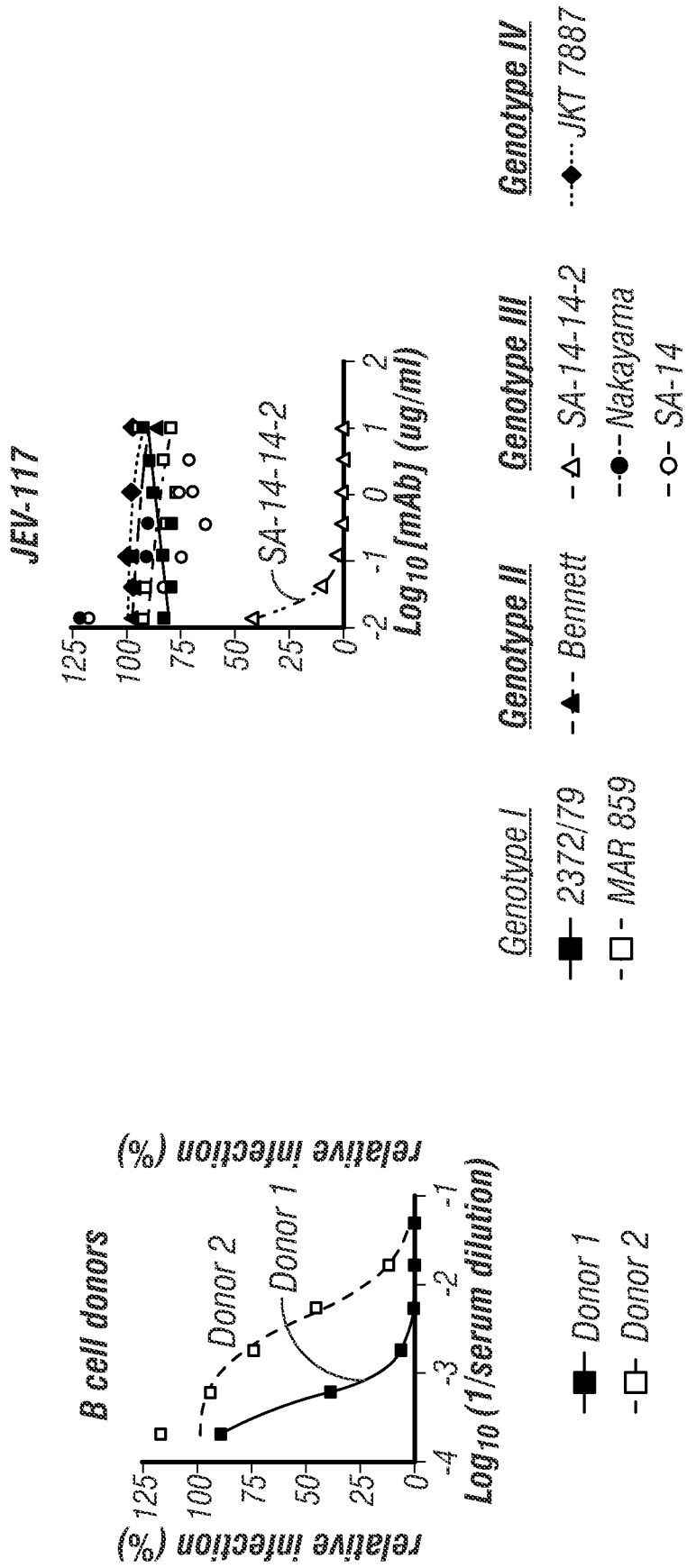
Figure 1B:
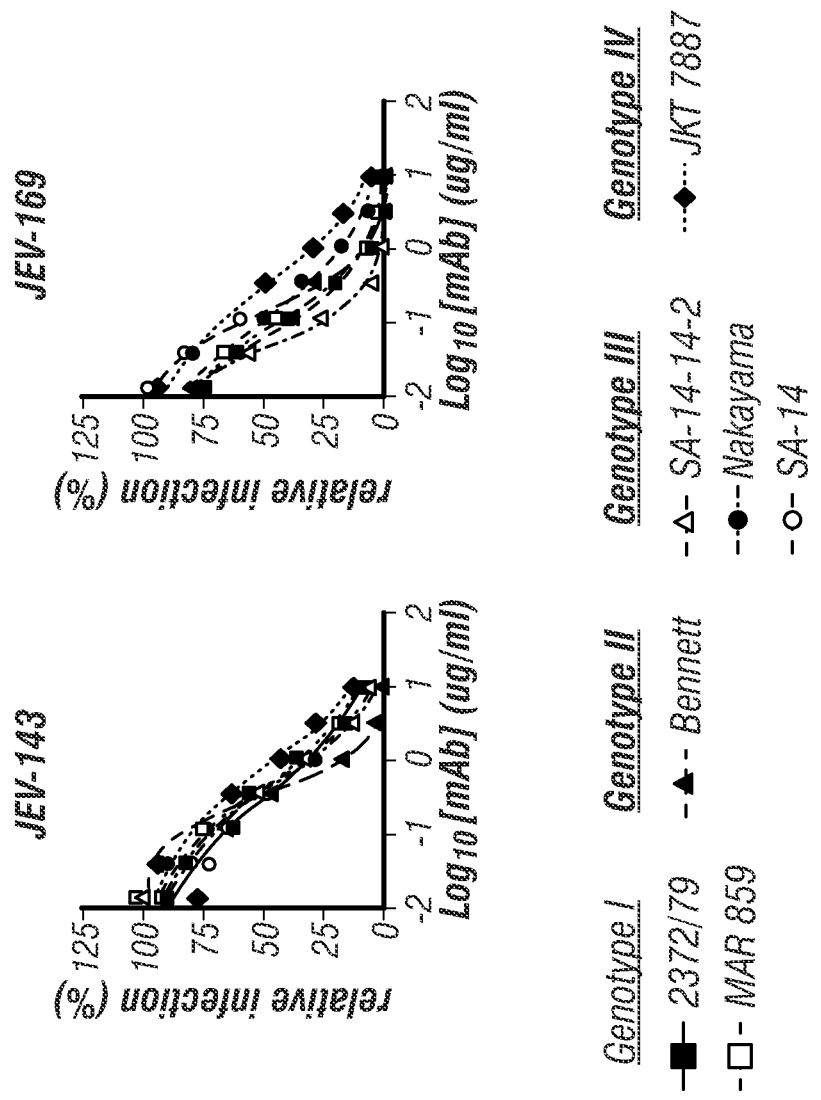

Although Japanese encephalitis virus (JEV) is a vaccine-preventable cause of viral encephalitis, the inactivated and live-attenuated platforms available are derived from strains belonging to a single genotype (genotype (G) III) due to its historical prevalence in epidemic areas. Related to this, studies with vaccines and antibodies have focused on assessing the in vitro and in vivo protective response to homologous or heterologous GIII strains. An epidemiologic shift in JEV genotype distribution warrants the induction of broadly neutralizing antibody responses that inhibit infection of multiple JEV genotypes. Here, a panel of human neutralizing monoclonal antibodies was generated and evaluated for their inhibitory activity, epitope location, and capacity for protection against multiple JEV genotypes in mice. These and other aspects of the disclosure are described in detail below.

I. JAPANESE ENCEPHALITIS VIRUS

Japanese encephalitis (JE) is an infection of the brain caused by the Japanese encephalitis virus (JEV). While most infections result in little or no symptoms, occasional inflammation of the brain occurs. In these cases, symptoms may include headache, vomiting, fever, confusion, and seizures. This occurs about 5 to 15 days after infection.

JEV is generally spread by mosquitoes, specifically those of the *Culex* type. Pigs and wild birds serve as a reservoir for the virus. The disease mostly occurs outside of cities. Diagnosis is based on blood or cerebrospinal fluid testing.

Prevention is generally with the Japanese encephalitis vaccine, which is both safe and effective. Other measures include avoiding mosquito bites. Once infected there is no specific treatment, with care being supportive. This is generally carried out in hospital. Permanent problems occur in up to half of people who recover from encephalopathy.

The disease occurs in Southeast Asia and the Western Pacific. About 3 billion people live in areas where the disease occurs. About 68,000 symptomatic cases occur a year with about 17,000 deaths. Often cases occur in outbreaks. The disease was first described in 1871. Japanese encephalitis (JE) is the leading cause of viral encephalitis in Asia, with up to 70,000 cases reported annually. Case-fatality rates range from 0.3% to 60% and depend on the population and age. Rare outbreaks in U.S. territories in the Western Pacific have also occurred. Residents of rural areas in endemic locations are at highest risk; Japanese encephalitis does not usually occur in urban areas.

Countries which have had major epidemics in the past, but which have controlled the disease primarily by vaccination, include China, South Korea, Japan, Taiwan and Thailand. Other countries that still have periodic epidemics include Vietnam, Cambodia, Myanmar, India, Nepal, and Malaysia. Japanese encephalitis has been reported in the Torres Strait Islands and two fatal cases were reported in mainland northern Australia in 1998. There were reported cases in Kachin State, Myanmar in 2013. The spread of the virus in Australia is of particular concern to Australian health officials due to the unplanned introduction of *Culex gelidus*, a potential vector of the virus, from Asia. However, the current presence on mainland Australia is minimal. There had been 116 deaths reported in Odisha's backward Malkangiri district of India in 2016.

Human, cattle, and horses are dead-end hosts as the disease manifests as fatal encephalitis. Swine acts as an amplifying host and has a very important role in the epidemiology of the disease. Infection in swine is asymptomatic, except in pregnant sows, when abortion and fetal abnormalities are common sequelae. The most important vector is *Culex tritaeniorhynchus*, which feeds on cattle in preference to humans. It has been proposed that moving swine away from human habitation can divert the mosquito away from humans and swine. The natural hosts of the Japanese encephalitis virus are birds, not humans, and many believe the virus will therefore never be completely eliminated. In November 2011, the Japanese encephalitis virus was reported in *Culex bitaeniorhynchus* in South Korea.

Recently whole genome microarray research of neurons infected with the Japanese Encephalitis virus has shown that neurons play an important role in their own defense against Japanese Encephalitis infection. Although this finding challenges the long-held belief that neurons are immunologically quiescent, an improved understanding of the proinflammatory effects responsible for immune-mediated control of viral infection and neuronal injury during Japanese Encephalitis infection is an essential step for developing strategies for limiting the severity of CNS disease.

A. Signs and Symptoms

The Japanese encephalitis virus (JEV) has an incubation period of 2 to 15 days and the vast majority of infections are asymptomatic: only 1 in 250 infections develop into encephalitis.

Severe rigors may mark the onset of this disease in humans. Fever, headache and malaise are other non-specific symptoms of this disease which may last for a period of between 1 and 6 days. Signs which develop during the acute encephalitic stage include neck rigidity, cachexia, hemiparesis, convulsions and a raised body temperature between 38-41° C. (100.4-105.8° F.). Mental retardation often develops.

Mortality of this disease varies but is generally much higher in children. Transplacental spread has been noted. Lifelong neurological defects such as deafness, emotional lability and hemiparesis may occur in those who have had central nervous system involvement. In known cases, some effects also include nausea, headache, fever, vomiting and sometimes swelling of the testicles.

Increased microglial activation following Japanese Encephalitis infection has been found to influence the outcome of viral pathogenesis. Microglia are the resident immune cells of the central nervous system (CNS) and have a critical role in host defense against invading microorganisms. Activated microglia secrete cytokines, such as interleukin-1 (IL-1) and tumor necrosis factor alpha (TNF-α), which can cause toxic effects in the brain. Additionally, other soluble factors such as neurotoxins, excitatory neurotransmitters, prostaglandin, reactive oxygen, and nitrogen species are secreted by activated microglia.

In a murine model of JE, it was found that in the hippocampus and the striatum, the number of activated microglia was more than anywhere else in the brain closely followed by that in the thalamus. In the cortex, the number of activated microglia was significantly less when compared with other regions of the mouse brain. An overall induction of differential expression of proinflammatory cytokines and chemokines from different brain regions during a progressive Japanese Encephalitis infection was also observed.

Although the net effect of the proinflammatory mediators is to kill infectious organisms and infected cells as well as to stimulate the production of molecules that amplify the mounting response to damage, it is also evident that in a nonregenerating organ such as the brain, a dysregulated innate immune response would be deleterious. In JE the tight regulation of microglial activation appears to be disturbed, resulting in an autotoxic loop of microglial activation that possibly leads to bystander neuronal damage. In animals, key signs include infertility and abortion in pigs, neurological disease in horses and systemic signs including fever, lethargy and anorexia.

B. Causative Agent

JEV is a virus from the family Flaviviridae, part of the Japanese encephalitis serocomplex of 9 genetically and antigenically related viruses, some which are particularly severe in horses, and four known to infect humans including West Nile virus. The enveloped virus is closely related to the West Nile virus and the St. Louis encephalitis virus. The positive sense single-stranded RNA genome is packaged in the capsid which is formed by the capsid protein. The outer envelope is formed by envelope protein and is the protective antigen. It aids in entry of the virus into the inside of the cell. The genome also encodes several nonstructural proteins (NS1, NS2a, NS2b, NS3, N4a, NS4b, NS5). NS1 is produced as secretory form also. NS3 is a putative helicase, and NS5 is the viral polymerase. It has been noted that Japanese encephalitis infects the lumen of the endoplasmic reticulum (ER) and rapidly accumulates substantial amounts of viral proteins for the Japanese Encephalitis.

Based on the envelope gene, there are five genotypes (I-V). The Muar strain, isolated from a patient in Malaya in 1952, is the prototype strain of genotype V. Genotype IV appears to be the ancestral strain, and the virus appears to have evolved in the Indonesian-Malaysian region. The first clinical reports date from 1870, but the virus appears to have evolved in the mid-16th century. Over sixty complete genomes of this virus had been sequenced by 2010.

C. Diagnosis

Japanese encephalitis is diagnosed by commercially available tests detecting JE virus-specific IgM antibodies in serum and/or cerebrospinal fluid, for example by IgM capture ELISA. JE virus IgM antibodies are usually detectable 3 to 8 days after onset of illness and persist for 30 to 90 days, but longer persistence has been documented. Therefore, positive IgM antibodies occasionally may reflect a past infection or vaccination. Serum collected within 10 days of illness onset may not have detectable IgM, and the test should be repeated on a convalescent sample. For patients with JE virus IgM antibodies, confirmatory neutralizing antibody testing should be performed. Confirmatory testing in the US is only available at CDC and a few specialized reference laboratories. In fatal cases, nucleic acid amplification, and virus culture of autopsy tissues can be useful. Viral antigen can be shown in tissues by indirect fluorescent antibody staining.

D. Prevention and Treatment

Infection with Japanese encephalitis confers lifelong immunity. There are currently three vaccines available: SA14-14-2, IC51 (marketed in Australia and New Zealand as JESPECT and elsewhere as IXIARO) and ChimeriVax-JE (marketed as IMOJEV). All current vaccines are based on the genotype III virus.

A formalin-inactivated mouse-brain derived vaccine was first produced in Japan in the 1930s and was validated for use in Taiwan in the 1960s and in Thailand in the 1980s. The widespread use of vaccine and urbanization has led to control of the disease in Japan, Korea, Taiwan, and Singapore. The high cost of this vaccine, which is grown in live mice, means that poorer countries have not been able to afford to give it as part of a routine immunization program.

The most common adverse effects are redness and pain at the injection site. Uncommonly, an urticarial reaction can develop about four days after injection. Vaccines produced from mouse brain have a risk of autoimmune neurological complications of around 1 per million vaccinations. However, where the vaccine is not produced in mouse brains but in vitro using cell culture there is little adverse effects compared to placebo, the main side effects are headache and myalgia.

The neutralizing antibody persists in the circulation for at least two to three years, and perhaps longer. The total duration of protection is unknown, but because there is no firm evidence for protection beyond three years, boosters are recommended every three years for people who remain at risk. Furthermore, there is also no data available regarding the interchangeability of other JE vaccines and IXIARO.

There is no specific treatment for Japanese encephalitis and treatment is supportive, with assistance given for feeding, breathing or seizure control as required. Raised intracranial pressure may be managed with mannitol. There is no transmission from person to person and therefore patients do not need to be isolated.

A breakthrough in the field of Japanese encephalitis therapeutics is the identification of macrophage receptor involvement in the disease severity. A recent report of an Indian group demonstrates the involvement of monocyte and macrophage receptor CLEC5A in severe inflammatory response in Japanese Encephalitis infection of the brain. This transcriptomic study provides a hypothesis of neuroinflammation and a new lead in development of appropriate therapeutic against Japanese encephalitis.

A number of drugs have been investigated to either reduce viral replication or provide neuroprotection in cell lines or studies upon mice. None are currently advocated in treating human patients.

The use of rosmarinic acid, arctigenin, and oligosaccharides with degree of polymerization 6 from *Gracilaria* sp. or *Monostroma nitidum* have been shown to be effective in a mouse model of Japanese encephalitis.

Curcumin has been shown to impart neuroprotection against Japanese Encephalitis infection in an in vitro study. Curcumin possibly acts by decreasing cellular reactive oxygen species level, restoration of cellular membrane integrity, decreasing pro-apoptotic signaling molecules, and modulating cellular levels of stress-related proteins. It has also been shown that the production of infective viral particles from previously infected neuroblastoma cells are reduced, which is achieved by the inhibition of ubiquitin-proteasome system.

Minocycline in mice resulted in marked decreases in the levels of several markers, viral titer, and the level of proinflammatory mediators and also prevents blood brain barrier damage.

II. MONOCLONAL ANTIBODIES AND PRODUCTION THEREOF

A. General Methods

It will be understood that monoclonal antibodies binding to Japanese Encephalitis virus will have several applications. These include the production of diagnostic kits for use in detecting and diagnosing Japanese Encephalitis virus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

In the case of human antibodies against natural pathogens, a suitable approach is to identify subjects that have been exposed to the pathogens, such as those who have been diagnosed as having contracted the disease, or those who have been vaccinated to generate protective immunity against the pathogen. Circulating anti-pathogen antibodies can be detected, and antibody producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. In one aspect, there are provided monoclonal antibodies having clone-paired CDR's from the heavy and light chains as illustrated in Tables 3 and 4, respectively. Such antibodies may be produced by the clones discussed below in the Examples section using methods described herein.

In a second aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies were generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Beltramello et al. (2010) previously reported the modification of neutralizing mAbs, due to their tendency to enhance DV infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four DENV serotypes. LALA variants retained the same neutralizing activity as unmodified mAbs but were completely devoid of enhancing activity. LALA mutations of this nature are therefore contemplated in the context of the presently disclosed antibodies.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. 5×10$^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF JAPANESE ENCEPHALITIS VIRUS INFECTION

A. Formulation and Administration

The present disclosure provides pharmaceutical compositions comprising anti-Japanese Encephalitis virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines are also envisioned where antibodies like those disclosed are produced in vivo in a subject at risk of Japanese Encephalitis virus infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, or by nebulizer. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnetate with stannous solution, chelating the reduced technetium onto a Sephadex column and applying the antibody to this column. Alternatively, direct labeling techniques may be used, e.g., by incubating pertechnetate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugate contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting Japanese Encephalitis virus and its associated antigens. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Other immunodetections methods include specific assays for determining the presence of Japanese Encephalitis virus in a subject. A wide variety of assay formats are contemplated, but specifically those that would be used to detect Japanese Encephalitis virus in a fluid obtained from a subject, such as saliva, blood, plasma, sputum, semen or urine. In particular, semen has been demonstrated as a viable sample for detecting Japanese Encephalitis virus (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may advantageously for formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of Japanese Encephalitis virus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing Japanese Encephalitis virus and contacting the sample with a first antibody in accordance with the present disclosure, as the case may be, under conditions effective to allow the formation of immunocomplexes.

These methods include methods for purifying Japanese Encephalitis virus or related antigens from a sample. The antibody will preferably be linked to a solid support, such as in the form of a column matrix, and the sample suspected of containing the Japanese Encephalitis virus or antigenic component will be applied to the immobilized antibody. The unwanted components will be washed from the column, leaving the Japanese Encephalitis virus antigen immunocomplexed to the immobilized antibody, which is then collected by removing the organism or antigen from the column.

The immunobinding methods also include methods for detecting and quantifying the amount of Japanese Encephalitis virus or related components in a sample and the detection and quantification of any immune complexes formed during the binding process. Here, one would obtain a sample suspected of containing Japanese Encephalitis virus or its antigens and contact the sample with an antibody that binds Japanese Encephalitis virus or components thereof, followed by detecting and quantifying the amount of immune complexes formed under the specific conditions. In terms of antigen detection, the biological sample analyzed may be any sample that is suspected of containing Japanese Encephalitis virus or Japanese Encephalitis virus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to Japanese Encephalitis virus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the Japanese Encephalitis virus or Japanese Encephalitis virus antigen is added to the wells. After binding and washing to remove non-specifically bound immune complexes, the bound antigen may be detected. Detection may be achieved by the addition of another anti-Japanese Encephalitis virus antibody that is linked to a detectable label. This type of ELISA is a simple "sandwich ELISA." Detection may also be achieved by the addition of a second anti-Japanese Encephalitis virus antibody, followed by the addition of a third antibody that has binding affinity for the second antibody, with the third antibody being linked to a detectable label.

In another exemplary ELISA, the samples suspected of containing the Japanese Encephalitis virus or Japanese Encephalitis virus antigen are immobilized onto the well surface and then contacted with the anti-Japanese Encephalitis virus antibodies of the disclosure. After binding and washing to remove non-specifically bound immune complexes, the bound anti-Japanese Encephalitis virus antibodies are detected. Where the initial anti-Japanese Encephalitis virus antibodies are linked to a detectable label, the immune complexes may be detected directly. Again, the immune complexes may be detected using a second antibody that has binding affinity for the first anti-Japanese Encephalitis virus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of Japanese Encephalitis virus antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled Japanese Encephalitis virus monoclonal antibodies to determine the amount of Japanese Encephalitis virus antibodies in a sample. The basic format would include contacting a known amount of Japanese Encephalitis virus monoclonal antibody (linked to a detectable label) with Japanese Encephalitis virus antigen or particle. The Japanese Encephalitis virus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many lab-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically, there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect Japanese Encephalitis virus or Japanese Encephalitis virus antigens, the antibodies may be included in the kit. The immunodetection kits will thus comprise, in suitable container means, a first antibody that binds to Japanese Encephalitis virus or Japanese Encephalitis virus antigen, and optionally an immunodetection reagent.

In certain embodiments, the Japanese Encephalitis virus antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the Japanese Encephalitis virus or Japanese Encephalitis virus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity, and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

VI. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Viruses. JEV strains 2372/79 (Thailand 1979, GenBank U70401), MAR 859 (Cambodia 1967, GenBank U70410), Bennett (Korea 1951, GenBank HQ223285), Nakayama (Japan 1935, GenBank EF571853), SA-14-14-2 (China 1954, GenBank JN604986), SA-14 (China 1954, GenBank M55506), and JKT 7887 (Indonesia 1981, L42160) were provided by the World Reference Center for Emerging Viruses and Arboviruses (K. Plante, S. Weaver, and R. Tesh, Galveston, TX). Virus stocks were propagated in C6/36 *Aedes albopictus* cells for 5 days prior to collection and titered by focus-forming assay (FFA) on Vero cell monolayers, as described (Brien et al., 2013).

MAb Generation. The human donors used in this study were born in the United States and Columbia and had not experienced JEV infection. However, they were not tested for prior exposure to other flaviviruses (e.g., WNV or DENV). Donors were immunized voluntarily with a two-dose regimen of a commercially-available inactivated JEV vaccine IXIARO® as part of an occupational exposure program. Peripheral blood was obtained for research purposes after informed consent approximately one month after boosting, with prior Institutional Review Board approval from Vanderbilt University Medical Center. Peripheral blood mononuclear cells (PBMCs) from heparinized blood were isolated using Ficoll-Histopaque and density gradient centrifugation. The cells were cryopreserved in the vapor phase of liquid nitrogen until use. Ten million PBMCs were cultured in 384-well plates (Nunc) using culture medium (ClonaCell-HY Medium A, StemCell Technologies) supplemented with 8 μg ml$^{-1}$ of the TLR agonist CpG (phosphorothioate-modified oligodeoxynucleotide ZOEZOEZZZZ-ZOEEZOEZZZT (SEQ ID NO: 49), Invitrogen), 3 μg ml$^{-1}$ of Chk2 inhibitor (Sigma™), 1 μg ml$^{-1}$ of cyclosporine A (Sigma™) and clarified supernatants from cultures of B95.8 cells (ATCC) containing Epstein-Barr virus. After 7 days, cells from each 384-well culture plate were expanded into four 96-well culture plates (Falcon™) using ClonaCell-HY Medium A containing 8 μg ml$^{-1}$ of CpG, 3 μg ml$^{-1}$ of Chk2 inhibitor, and 10$^7$ irradiated heterologous human PBMCs (Nashville Red Cross) and cultured for an additional 4 days. Supernatants were screened in ELISA (described below) for reactivity with JEV-SA-14-14-2. Hybridoma cell lines were cloned by single-cell flow cytometric sorting in a sterile FACSAria III cytometer (BDBiosciences™).

Neutralization assays. Serial dilutions of mAbs were incubated with 10$^2$ FFU of different JEV strains for 1 h at 37° C. as described previously (Brien et al., 2013). MAb-virus complexes were added to Vero cell monolayers for 1 h at 37° C. followed by a 1% (w/v) methylcellulose in Modified Eagle Medium (MEM) supplemented with 4% FBS. Plates were fixed and processed as described in a preceding section. Non-linear regression analysis was performed, and EC$^{50}$ values were calculated after comparison to wells infected with JEV in the absence of mAb.

Flavivirus E ectodomain, JEV E-DI and JEV E-DIII expression and purification. JEV envelope (E) protein (residues 1 to 399 corresponding to the E ectodomain of the JEV-SA14-14-2 strain) was prepared as previously described (Luca et al., 2012). A JEV E-DI synthetic gene was designed based on a DENV-4 DI construct (Cockburn et al., 2012) with modifications such that JEV E residues 1-50 were linked to residues 135-195 by a glycine dipeptide, and residues 135-195 were connected by a serine residue to residues 281-298. This fragment was cloned into the pFM1.2 mammalian expression vector (Cockburn et al., 2012) downstream of a pHLsec signal sequence and terminated with a C433 terminal tobacco etch virus (TEV) protease and hexahistidine affinity tag. Transient expression and purification was completed using established protocols (Zhao et al., 2016). JEV E-DIII (residues 299-399) was cloned into the NdeI and XhoI restriction enzyme sites of pET21a for expression in BL21 (DE3) codon plus E. coli cells by autoinduction (Studier, 2005). The protein was refolded from inclusion bodies and purified by size-exclusion essentially as described (Edeling et al., 2014). WNV (Nybakken et al., 2006) and ZIKV (Zhao et al., 2016) E ectodomain proteins were produced and purified based on established protocols.

JEV mAb domain mapping. MaxiSorp 96-well plates (ThermoFisher™) was coated with 440 50 μl of 4 μg/mL of recombinant JEV E (Luca et al., 2012), JEV E-DI, JEV E-DIII, WNV E, or ZIKV E overnight at 4° C. Plates were washed three times with PBS with 0.02% Tween-20 followed by incubation with PBS and 2% BSA for 1 h at 37° C. MAbs were added (1 μg/ml) for 1 h at room temperature. Plates were washed again and sequentially incubated with biotin-conjugated anti-mouse IgG, Streptavidin-HRP, and TMB-substrate. The reaction was stopped by addition of 2 M H$_2$SO$_4$, and emission (450 nm) was read using a TriStar LB 941 reader (Berthold Technologies).

Pre- and post-attachment neutralization assays. For pre-attachment assays, serial dilutions of mAbs were prepared at 4° C. in DMEM with 2% FBS and pre-incubated with 10$^2$ FFU of JEV-SA-14-14-2 for 1 h at 4° C. MAb-virus complexes were added to a monolayer of Vero cells for one hour at 4° C. Unbound virus was removed with three washes of chilled DMEM and adsorbed virus was allowed to internalize during a 37° C. incubation for 1 h. Cells were overlaid with 1% (w/v) methylcellulose in MEM supplemented 451 with 4% FBS. For post-attachment assays, 10$^2$ FFU of JEV-SA-14-14-2 was adsorbed onto a monolayer of Vero cells for one hour at 4° C. After removing unbound virus, serial dilutions of mAbs were added to virus-absorbed cells for 1 h at 4° C. Virus then was allowed to internalize for 1 h at 37° C., and subsequently cells were overlaid with methylcellulose as described above. Thirty hours later, the plates were fixed with 2% PFA and analyzed for antigen-specific foci as described above.

Fusion blockade assay. The assay for plasma membrane fusion inhibition with flavivirus mAbs has been described (Pal et al., 2013, Thompson et al., 2009 and Liao and Kielian, 2005). Briefly, Vero cells (2×10$^4$ per well) were seeded at in a flat-bottom 96-well plates overnight at 37° C. The following day, cells were pre-incubated with 10 nM concanamycin A (Sigma™ Cat #C9705), which blocks acidification of endosomes and viral fusion, for 30 min on ice and subsequently incubated with JEV-SA-14 (MOI of 50) for 2 h. Cells were washed twice with chilled PBS followed by incubation with 50 μg/ml (human) mAbs for 30 min on ice. Cells were pH-shifted with warmed DMEM (buffered to pH 5.5 or control pH 7.5) at 37° C. for ~7 min. The cells were rinsed and incubated for 24 h at 37° C. in DMEM with 10 nM concanamycin A. Subsequently, cells were rinsed, fixed, permeabilized, and sequentially stained for 1 h at 4° C. with JEV-13 (1 μg/ml) and goat anti-mouse AlexaFluor-conjugated secondary (1:2,000). Samples were processed by flow cytometry (MacsQuant) and data was analyzed using FlowJo software.

Hydrogen-deuterium exchange. Continuous HDX labeling of JEV E-DIII with or without the mAbs were performed at 25° C. for 0, 10, 30, 60, 120, 900, 3,600 and 14,400 seconds as previously described with the following modifications (Yan et al., 2015). Briefly, stock solutions of both JEV E472 DIII with or without the mAbs were prepared in PBS pH 7.4 and incubated at 25° C. for at least 1 h. Continuous labeling with deuterium was initiated by diluting the stock samples 10-fold in deuterated PBS buffer (Sigma-Aldrich™). HDX control samples (non-deuterated) were prepared in the same way with H$_2$O. Quenching was performed under reducing condition by adding a solution of 500 mM Tris (2-carboxyethyl)phosphine 476 hydrochloride (TCEP HCl) and 4M guanidine hydrochloride in PBS buffer pH 7.4 (adjusted using sodium hydroxide) to the reaction vial at a 1:1 volume ratio. The sample was mixed and incubated for a minute at 25° C. before loading on to a custom-built HDX platform for desalting, on-line pepsin digestion, and reversed-phase separation and directly injected into the mass spectrometer for analysis. The sample was passed over a custom-packed 2×20 mm pepsin column at 200 μL/min; immobilized pepsin was prepared according to a published protocol (Busby et al., 2007). The peptides resulting from digestion were captured by a 2.1×20 mm Zorbax Eclipse XDB-C8 trap column (Agilent) and desalted at 200 µL/min of H$_2$O containing 0.1% triflouroacetic acid for 3 min. The peptides were separated by a 2.1×50 mm C18 column (2.5 µm XSelect CSH C18; Waters) with a 9.5-min gradient of 5%-100% acetonitrile in 0.1% formic acid at a flow rate of 100 µl/min delivered by a LEAP 3×Ti pump (LEAP technologies, NC). The linear part of the gradient from 0.3 min to 5.5 min raised the acetonitrile content from 15% to 50%, during which time most of the peptides eluted from the C18 column. The entire fluidic system was kept in an ice bath except for the pepsin column to minimize back exchange. Duplicate measurements were carried out for each of the time points.

Site-directed mutagenesis epitope mapping. Epitope mapping was performed by alanine-scanning mutagenesis as described previously (Davidson and Doranz, 2014). A JEV prM-E protein expression construct (based on JEV-SA-14-14-2) was subjected to commercial alanine scanning mutagenesis (Geneweiz) to generate a mutant library. Each residue within the JEV E protein was changed to alanine, with alanine codons mutated to serine and cysteine residues left unchanged. In total, 400 mutants were generated and sequence confirmed. Each JEV E protein mutant was transfected into human 293T cells and allowed to express for 24 h, and then fixed and permeabilized with Foxp3 transcription factor staining buffer (Thermo™ #00-5523-00). Cells were incubated sequentially with purified mAbs at concentrations optimized for staining (range 30-1,000 ng/ml) and AlexaFluor647-conjugated secondary antibody (Invitrogen) in permeabilization buffer. Fluorescence signal was detected by flow cytometry (MacsQuant) and analyzed using FlowJo software. Antibody reactivity against each mutant was compared to the WT prM-E protein after subtracting signal from mock-transfected controls and normalizing to the signal from WT prM-E transfected controls. Mutations were identified as critical to the mAb epitope if they showed less than 25% binding compared to wild-type. For charge mutants, residues were substituted in the A-strand (S309K, K312E, and H395K), DIII-LR (S331K, S364K, N367K, and K369E), C-C' loop (T349K), and FG loop (R387E and D389K) and transfected and stained as described above.

Mouse experiments. Animal studies were carried in accordance with the recommendations of the Guide for the Care and Use of Laboratory Animals of the National Institutes of Health and were approved by the Institutional Animal Care and Use Committee at the Washington University School of Medicine (Assurance number A3381-01). Mice were inoculated with JEV after induction of anesthesia using ketamine hydrochloride and xylazine, and all efforts were made to minimize 528 pain and suffering. Antibody protection studies were performed in the following models:
  (a) Genotype I. WT C57BL/6 male mice (3 week-old, Jackson Laboratories) were inoculated with 10$^3$ FFU of JEV-MAR 859 or JEV-2372/79 via a subcutaneous route in the footpad. Anti-JEV or isotype control (CHK-152) mAbs were administered by intraperitoneal route as a single dose at day −1 (10 µg, 0.5 mg/kg) or day +5 (250 µg, 12.5 mg/kg) after infection. Animals were monitored for lethality for 28 days.
  (b) Genotype III. WT C57BL/6 male mice (4-5 week-old, Jackson Laboratories) were inoculated with 10$^2$ FFU of JEV-Nakayama by subcutaneous route in the footpad. Anti-JEV or isotype control (CHK-152) mAbs were administered by intraperitoneal route as a single dose at day −1 (10 µg, 0.5 mg/kg) or day +5 (250 µg, 12.5 mg/kg) after infection. Animals were monitored for lethality for 28 days.

Statistical analysis. Statistical significance of FFWO was determined by one-way ANOVA with Dunnett's multiple comparisons to isotype-control mAb. Statistical significance of alanine shotgun mutagenesis was determined by one-way ANOVA with Holm-Sidak's multiple comparisons of each mutant to V315 for each mAb. Kaplan-Meier survival curves were analyzed by the log-rank test for each mAb compared to isotype-control mAb.

Example 2—Results

To generate human mAbs against JEV, neutralization profiles were screened from donors immunized with a two-dose regimen of a commercially-available inactivated JEV vaccine IXIARO® that was based on a genotype III strain (FIGS. 1A-B). Hybridoma supernatants derived from donors that bound to JEV-SA14-14-2 were obtained, determined single end-point neutralization titer (data not shown), and cloned 4 anti-JEV mAbs. Three of the human mAbs bound to E-DIII whereas hJEV-75 bound to the E ectodomain but not to E-DI or E-DIII (Table 5). hJEV-11 and hJEV-80 cross-reacted with WNV E protein whereas hJEV-69 and hJEV-75 appeared specific to JEV and did not bind either WNV or ZIKV E proteins.

Figure 1C:
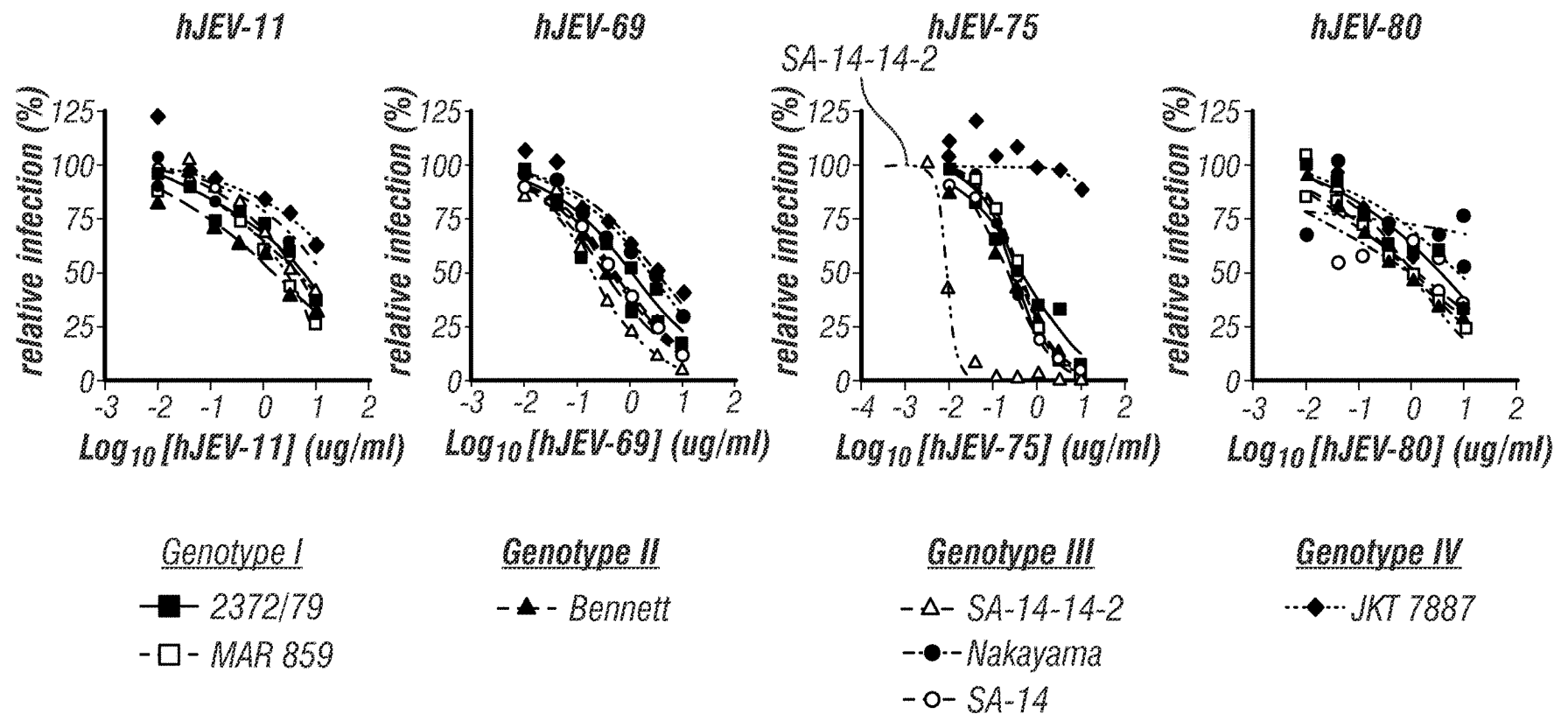

Breadth of neutralization of mAbs. Focus reduction neutralization tests (FRNT) were performed on Vero cells to assess the inhibitory capacity of anti-JEV mAbs against the vaccine strain, JEV-SA-14-14-2, and available prototype strains representative of multiple genotypes. They did not test a representative genotype V strain of JEV, as one was not available from the World Arbovirus Reference Collection. They determined the mAb concentration that reduced the number of foci of infection by 50% (EC$_{50}$ values, FIG. 1C and Table 5). Four human mAbs with neutralizing activity against JEV-SA-14-14-2 were identified and characterized in greater detail. hJEV-11 and hJEV-80 exhibited relatively weak neutralizing activity (1,509-10,000 ng/ml and 857-10,000 ng/ml, respectively) against the other strains tested (FIG. 1C and Table 5). In comparison, hJEV-69 and hJEV-75 inhibited infection of multiple JEV strains more potently. hJEV-69 had greater activity against the GI strains (2372/79 and MAR 859, EC$_{50}$=335-1102 ng/ml) than against the GIV strain (JKT 7887, EC$_{50}$=3,111 ng/ml) whereas hJEV-75 had the strongest neutralizing activity against GI, GII, and GIII strains (EC$_{50}$=9-457 ng/ml) but did not inhibit the GIV strain (JKT 7887, EC50 >10,000 ng/ml).

Figure 2A:
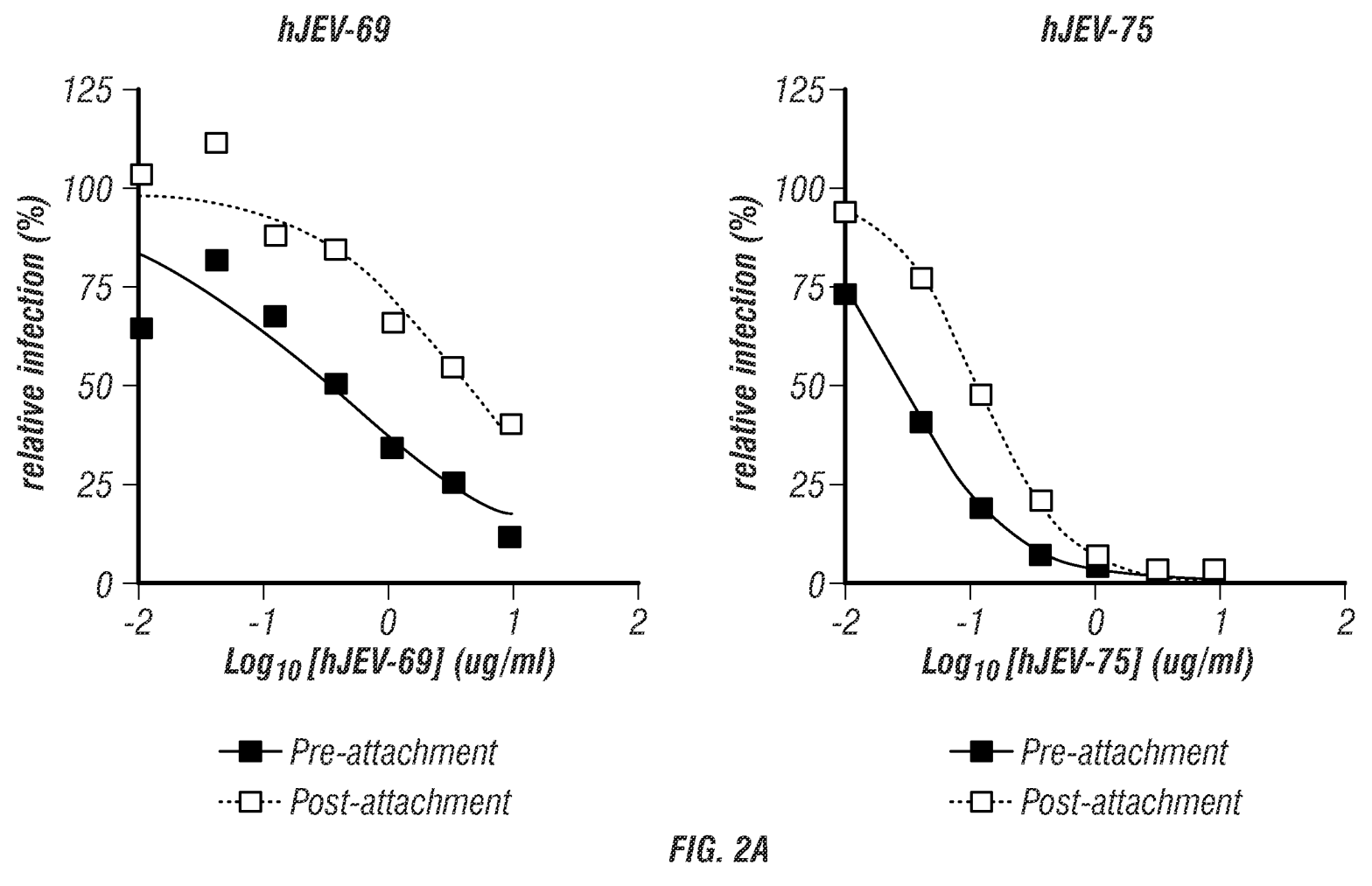

Mechanism of neutralization. Antibody neutralization of flaviviruses can occur by inhibiting attachment, internalization, and/or fusion (Pierson et al., 2008). To determine how the neutralizing mAbs inhibited infection in cell culture, pre- and post-attachment neutralization assays were performed (Pal et al., 2013, Thompson et al., 2009 and Liao and Kielian, 2005). MAbs were incubated with JEV-SA-14-14-2 before or after virus binding to cells, and infection was measured by FRNT (Pal et al., 2013, Thompson et al., 2009 and Liao and Kielian, 2005). hJEV-69 and hJEV-75 neutralized in both pre- and post-attachment assays (FIG. 2A).

Figure 2B:
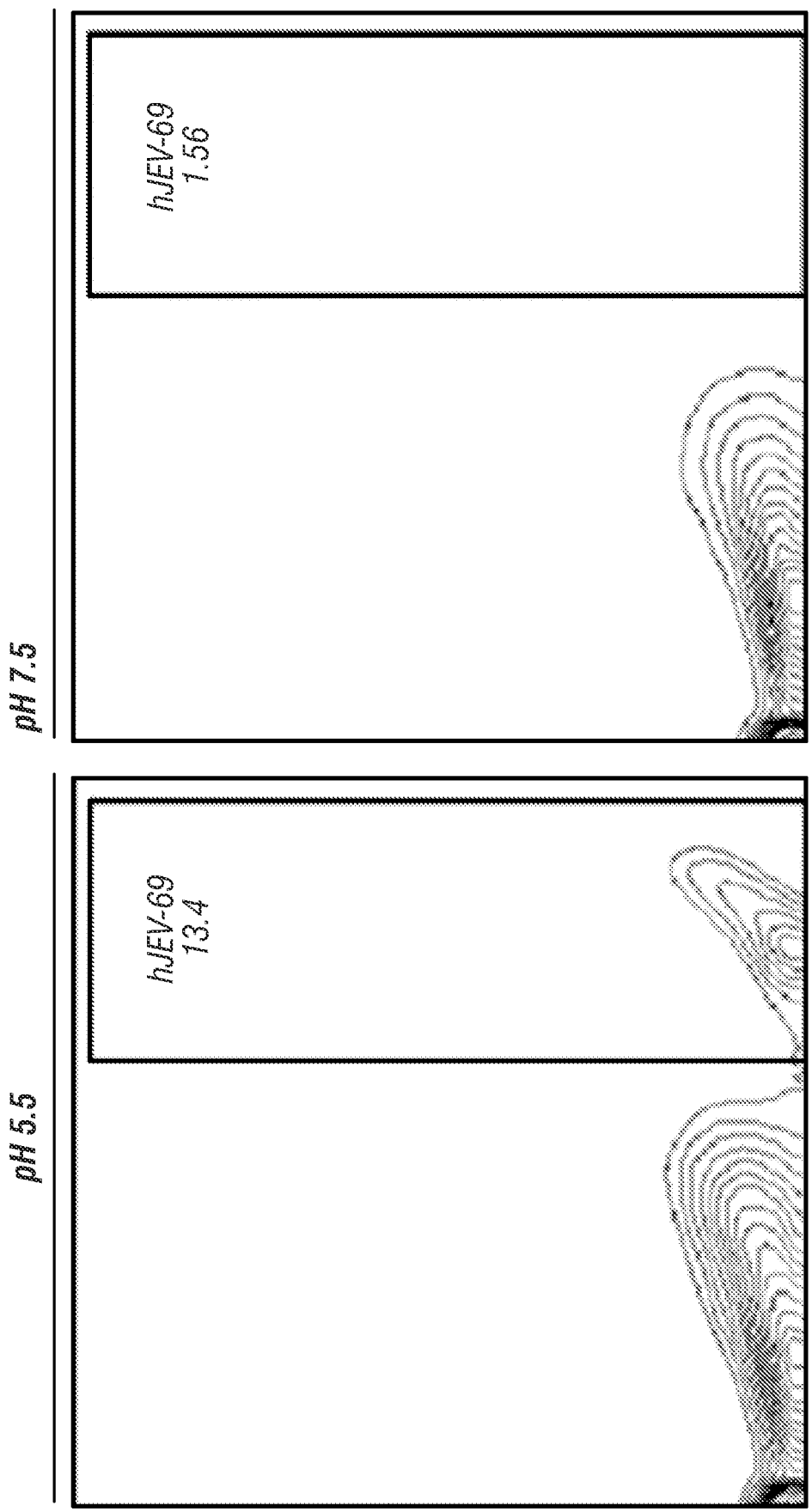

Next it was determined whether the neutralizing human mAbs could block fusion by adapting a virus fusion from without (FFWO) assay at the plasma membrane (Pal et al., 2013 and Thompson et al., 2009). JEV-SA-14 was adsorbed to a monolayer of Vero cells on ice and subsequently incubated with the mAbs. Fusion at the plasma membrane was induced by brief exposure to low pH-buffered medium at 37° C. After washing, cells were incubated overnight in the presence of 10 nM concanamycin A1 to prevent canonical endosomal fusion and allow viral replication. As described for other flaviviruses (Thompson et al., 2009), in the absence of mAb treatment, ~20% of cells produced viral antigen that was measurable by flow cytometry; in contrast, reduced viral antigen was detected when fusion was induced under neutral pH conditions with hJEV-69 and hJEV-75 (FIG. 2B).

Epitope mapping. To begin to assess the basis for differential inhibition by the neutralizing mAbs, their epitopes were mapped. Key peptide regions and amino acid residues required for mAb binding were defined by using both hydrogen-deuterium exchange mass spectrometry (HDX-MS) (Chen et al., 2016) and alanine-scanning site-directed mutagenesis (Davidson and Doranz, 2014) of the E protein of JEV-SA14-14-2.

Figure 3A:
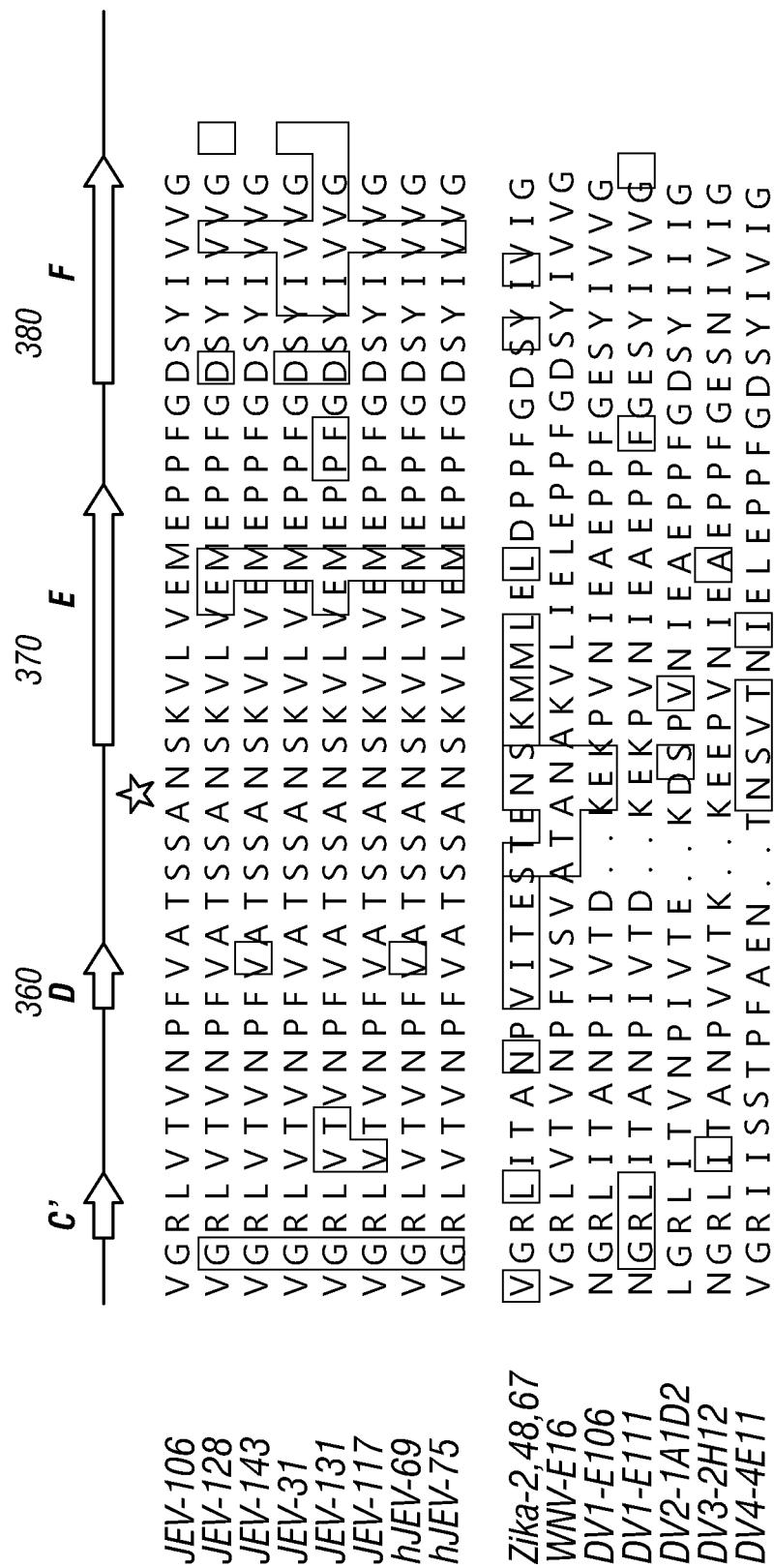
(FIG. 3A) JEV E-DIII epitopes for each of the human JEV mAbs were defined by alanine scanning mutagenesis (shaded gray box) and HDX (bold letters). Genotypic differences to the JEV-SA-14-14-2 strain (GIII) are highlighted by a star: V315 is A in JEV-2372/79 (GI), JEV-MAR 859 (GI), JEV-Bennett (GII), and JEV-Nakayama (GIII) strains; S327 is T in JEV-2372/79 (GI), JEV-MAR 859 (GI), and JEV-Bennett (GIII) strains; K336 is N in JEV-2372/79 (GI) and JEV-MAR 859 (GI) strains; and A366 is S in JEV-2372/79 (GI), JEV-MAR 859 (GI) and JEV-Bennett (GIII) strains. For comparison to the JEV E-DIII epitopes, immediately below the structurally defined E-DIII epitopes of ZIKV are shown in complex with ZV-2 (ABDE epitope), ZV-48 (C-C') and ZV-67 (lateral ridge, LR), WNV E16 (LR), DV1-E106 (LR), DV1-E111 (C-C' loop), DV2-1A1D-2 (A-strand), DV3-2H12 (AB-loop), and DV4-4E11 (A-strand). (Top to Bottom: JEV-106/JEV-128/JEV-143/JEV-31/JEV-131/JEV-117/hJEV-69/hJEV-75=SEQ ID NO: 41; Zika-2,48,67=SEQ ID NO: 42; WNV-E16=SEQ ID NO: 43; DV1-E106=SEQ ID NO: 44; DV1-E111=SEQ ID NO: 45; DV2-1A1D2=SEQ ID NO: 46; DV3-2H12=SEQ ID NO: 47; DV4-4E11=SEQ ID NO: 48) (FIG. 3B) JEV E-DIII epitopes defined by alanine scanning mutagenesis are depicted on the JEV E-DIII structure (based on the full-length JEV E structure, PDB code 3P54).
Figure 3A:
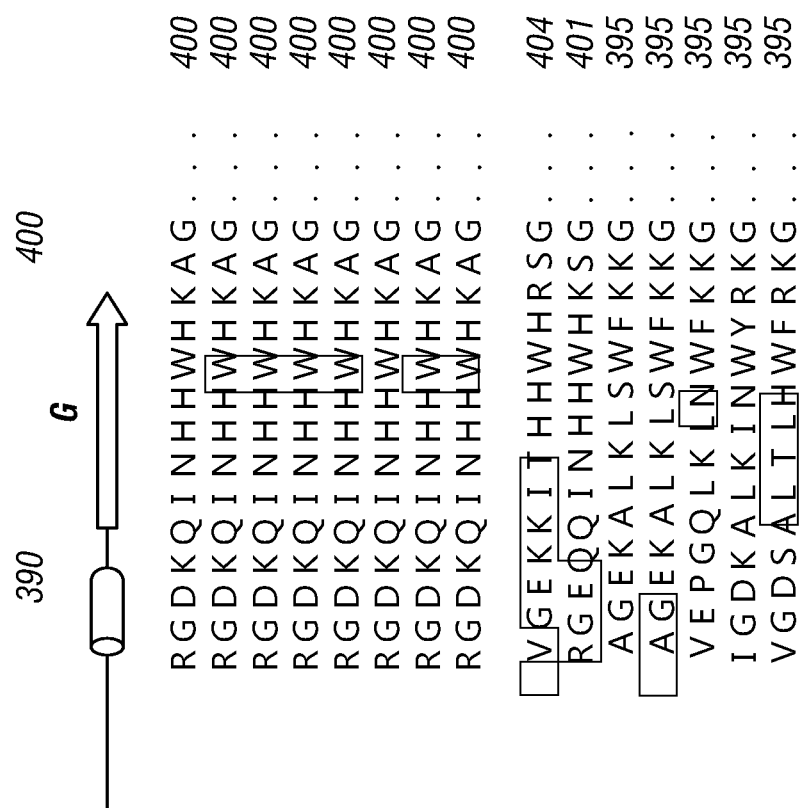
Figure 3B:
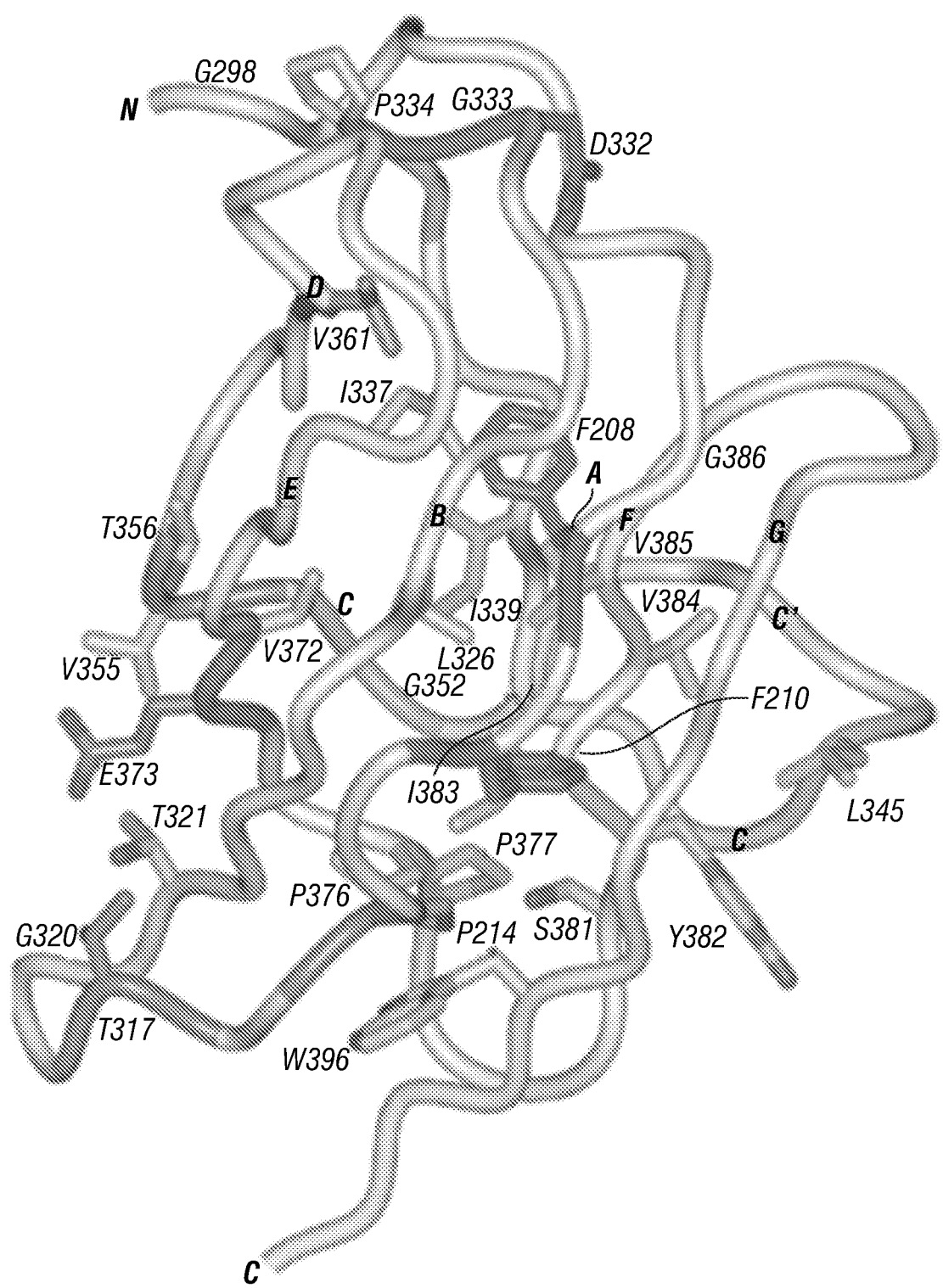
(FIG. 3C) JEV epitopes defined by alanine scanning mutagenesis (shown in the context of the full-length JEV E structure).
Figure 3C:
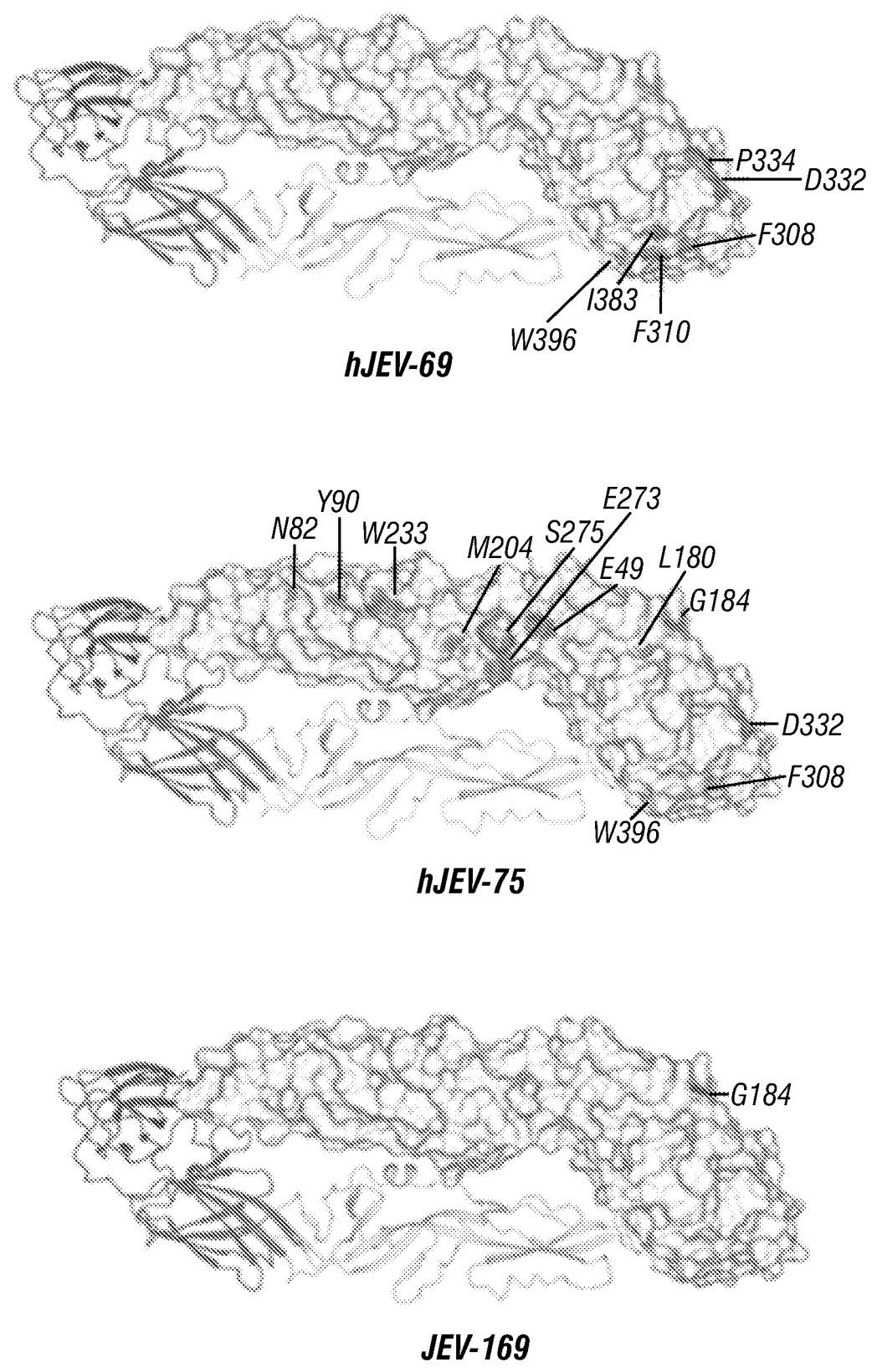

The amino acid binding sites of neutralizing human anti-JEV mAbs were mapped by alanine scanning mutagenesis and mammalian cell expression (Davidson and Doranz, 2014) of the JEV prM-E protein. Residues in the E protein ectodomain were substituted to alanine with two exceptions: alanine residues were mutated to serine, and cysteines were not mutated to prevent protein misfolding. A residue was characterized as critical for mAb binding if the mutation resulted in less than 25% binding compared to the wild-type protein (FIGS. 3A-C). It was found that alanine substitution of certain amino acids (e.g., T321, D332, and I383), which correspond to sites in E216 DIII-LR, caused loss of binding of most of the neutralizing human mAbs tested, especially hJEV-69 (FIG. 3B). hJEV-75 demonstrated loss of binding following mutations in other regions of the E ectodomain (FIG. 3C) that correspond to previously defined epitopes for related flavivirus including residues in the E-DI-DII hinge region (K136 for JEV-117 and S275 for hJEV-75), E-DI-LR (L180 for hJEV-75), E-DII-hinge (E49), E223 DII-LR (N82 for hJEV-75), and E-DII-central interface (W217 for hJEV-75) (Luca et al., 2012 and Oliphant et al., 2006). The loss of binding observed within E-DIII for alanine substitutions of residues F308 (JEV-117 and hJEV-75) and F310 (JEV-117) corresponds to sites within the previously described A-strand epitope (Sukupolvi-Petty et al., 2007). This pattern of mutagenesis and binding also correlates with the inability of hJEV-75 to recognize isolated domains by ELISA (Table 5).

Figure 4A:
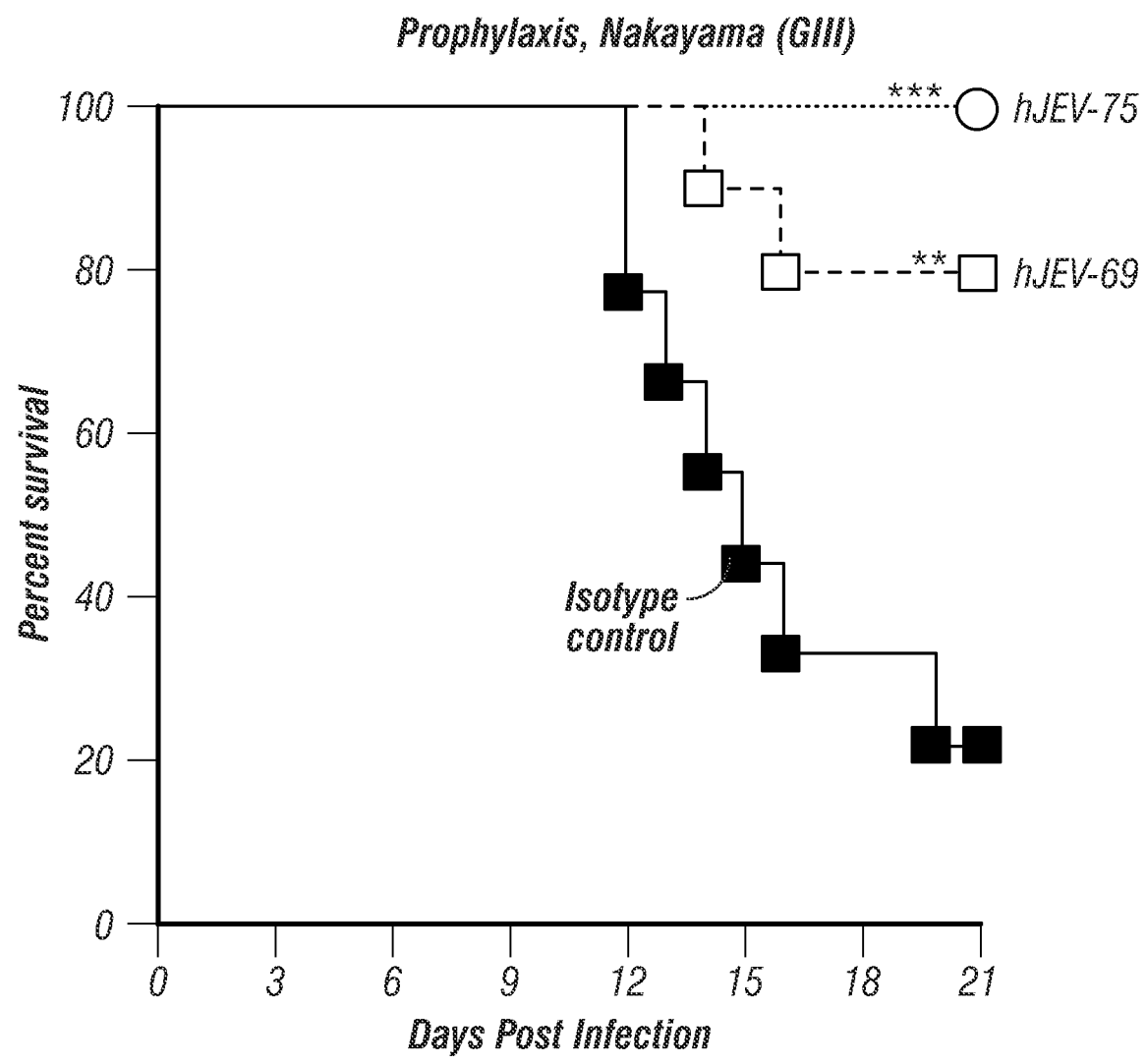
FIGS. 4A-C. Protective efficacy of anti-JEV mAbs in mice.
Figure 4B:
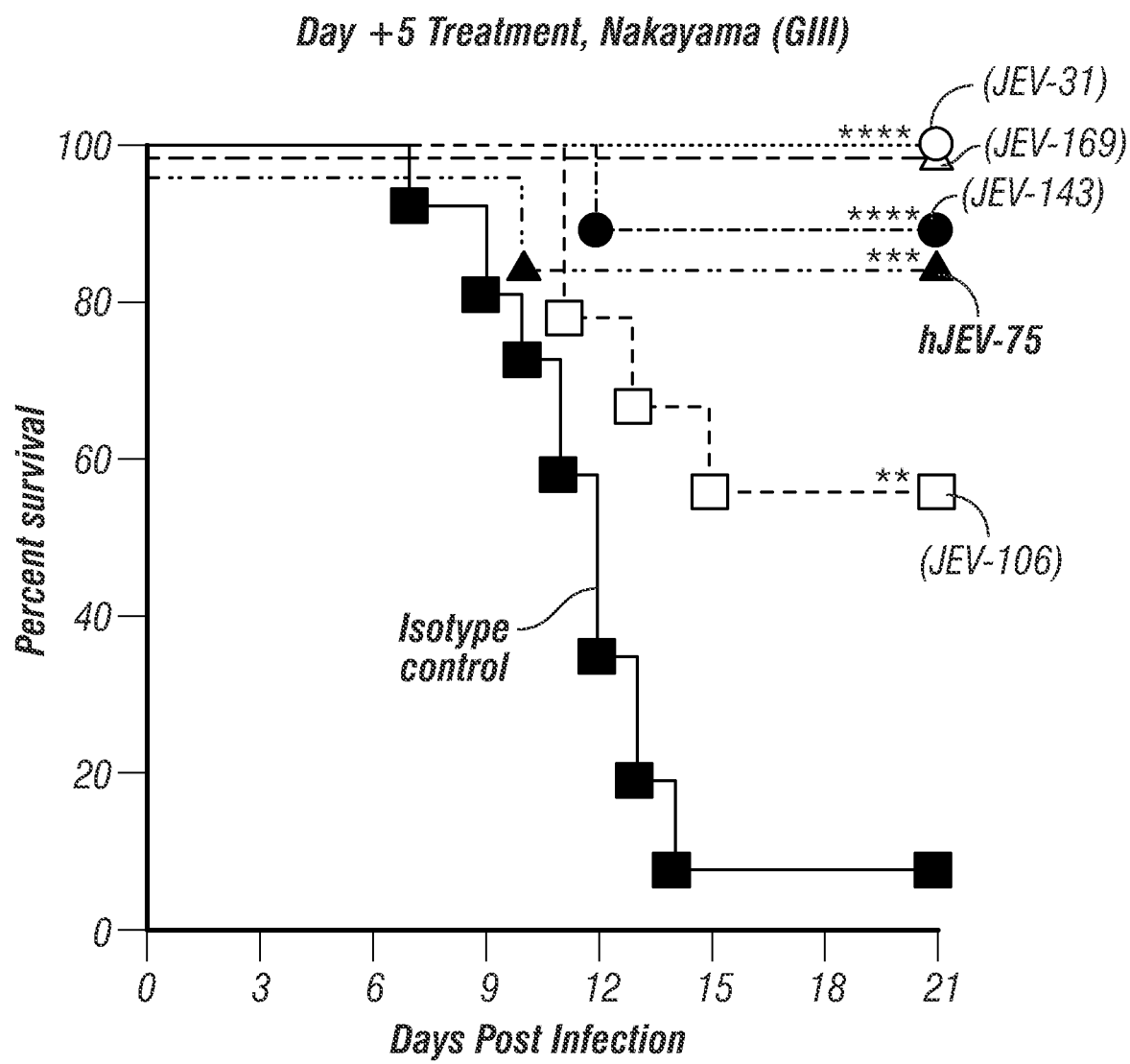
Figure 4C:
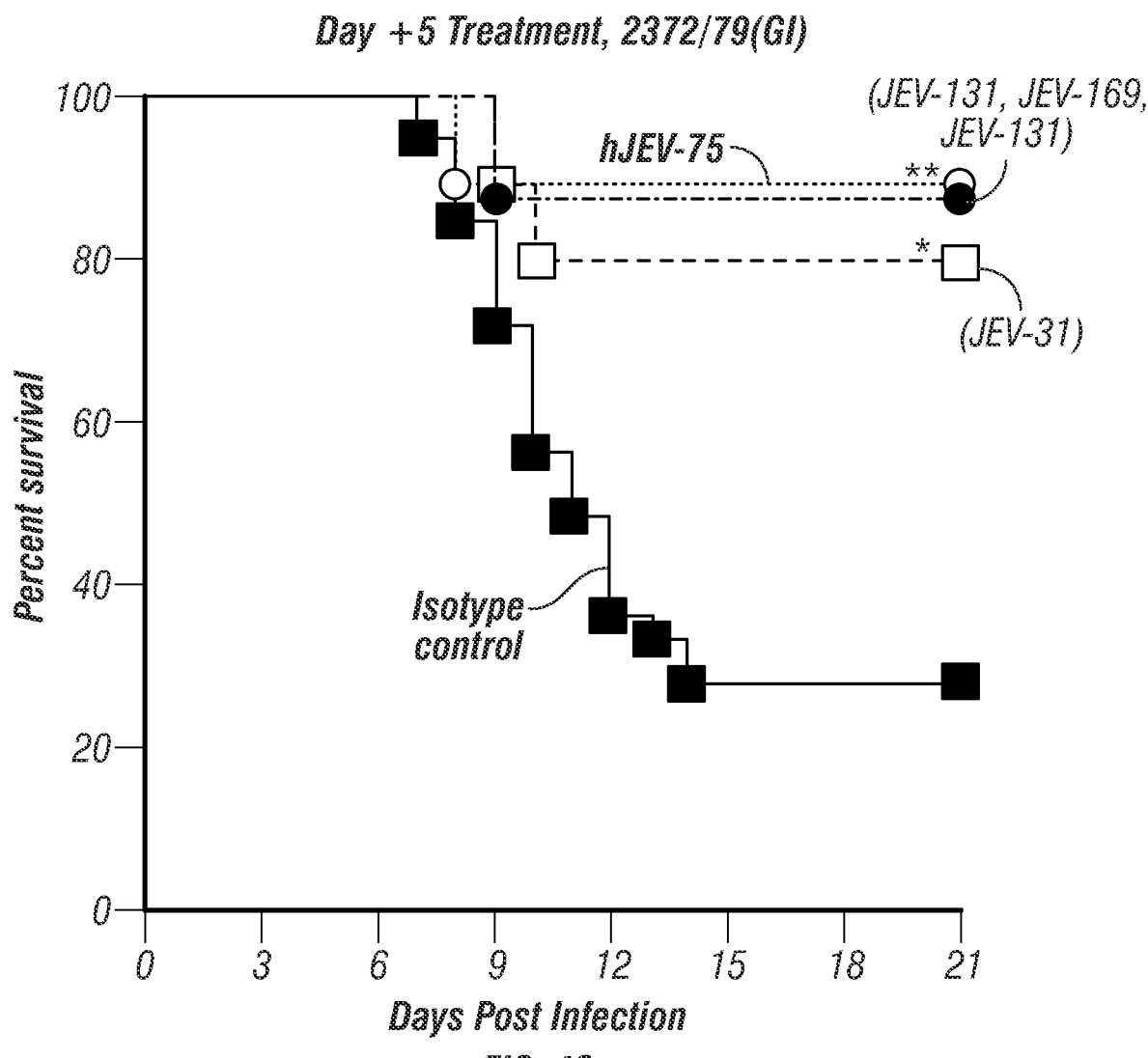

In vivo protection studies. To evaluate whether neutralizing mAbs could protect against JEV infection in vivo, challenge models of JEV-induced lethality in mice were used by using GIII (Nakayama) and GI (MAR 859 and 2372/79 strains). Once models were established, 4- to 5-week-old male WT C57BL/6 mice were treated at day −1 with a single 10 µg (0.5 mg/kg) prophylactic dose of different anti-JEV mAbs or an isotype-control mAb and then inoculated animals at day 0 with different pathogenic JEV strains. Protection (60 to 80%) against Nakayama, GIII was observed with hJEV-69 and hJEV-75 (FIG. 4A). Administration of hJEV-75 at 5 days after infection also had significant protection against both JEV-Nakayama (GIII) and JEV-2372/79 (GI) strains (FIGS. 4A and 4B). Overall, these data show that a single mAb that broadly neutralizes multiple JEV genotype can provide therapeutic activity in vivo against multiple strains.

TABLE 5

Binding and Neutralization of Inhibitory Anti-JEV mAbs

| Human | | | | GI | GII | | GIII | | GIV |
|---|---|---|---|---|---|---|---|---|---|
| hJEV-11 | hIgG1, κ | DIII | W | 5445 | 1509 | 4116 | >10,000 | 4528 | 2226 | >10,000 |
| hJEV-69 | hIgG1, κ | DIII | N | 1102 | 335 | 524 | 2444 | 475 | 211 | 3111 |
| hJEV-75 | hIgG1, λ | N | N | 457 | 228 | 388 | 294 | 414 | 9 | >10,000 |
| hJEV-80 | hIgG1, λ | DIII | W | 3371 | 1117 | 1036 | >10,000 | 857 | 1007 | 7733 |

Example 3—Discussion

The inventor sought to identify human mAbs that broadly neutralize infection of JEV strains corresponding to most genotypes. The first human mAbs for JEV ever reported were isolated from B cells of recipients of a chemically-inactivated JEV vaccine; to the inventor's knowledge, this also is the first isolation of human mAbs from an individual immunized with an inactivated flavivirus vaccine. He identified two strongly neutralizing JEV-specific human mAbs, one (hJEV-69) that recognized E-DIII-LR and another (hJEV-75) that mapped to residues in the E-DI-LR, E-DI-DII hinge, E-DII-LR, and E-DII hinge. Future studies will need to assess the inhibitory potential of the anti-JEV humoral response against contemporary strains of JEV of all genotypes, including GV strains.

Type-specific and cross-reactive neutralizing mAbs have been identified against JEV. Although others have identified E-DIII-specific anti-JEV mAbs from mice (Kimura-Kuroda and Yasui, 1986, Mason et al., 1989 and Lin et al., 2003), this class of antibodies appears less immunodominant in humans, at least against some (Beltramello et al., 2010, Jarmer et al., 2014, Smith et al., 2013, Robbiani et al., 2017 and Throsby et al., 2006) but not all (Vratskikh et al., 2013 and Wahala WMPB, Kraus A A, Haymore L B, Accavitti-Loper M A, De Silva A M. Dengue virus neutralization by human immune sera: role of envelope protein domain III—reactive antibody) flaviviruses. Murine-derived E-DIII specific mAbs (2H4, A3, E3.3) against JEV had stronger neutralizing activity in vitro than E-DII specific mAbs (Kimura-Kuroda and Yasui, 1986, Zhang et al., 1989, Kimura-Kuroda and Yasui, 1983 and Shimoda et al., 2013). Humanization of chimpanzee-derived E-DI (A3 and B2) 286 and E-DIII (E3) specific mAbs demonstrated equivalent in vitro neutralization compared to the parental mAbs, and this finding correlated with protection against JEV infection in mice by the homologous genotype (GIII) (Goncalvez et al., 2008).

mAb hJEV-75 identified residues across E-DI and E-DII, particularly within the previously defined E-DI-LR, E-DII-LR, and E-DI-DII hinge epitopes. Higher resolution studies, including X-ray crystallography and cryo-electron microscopy, are necessary to determine the precise geometry of binding and a complete footprint of interaction residues. hJEV-75 effectively neutralized the JEV-SA-14-14-2 vaccine strain but remarkably lost inhibitory activity against the parental JEV-SA-14 strain. This mAb mapped to an epitope that also contained residues outside of E-DIII, in E-DI and E-DII. An alignment of the genotypic variation in JEV sequences failed to show a direct correlation with the residues identified in loss of binding of studies for hJEV-75. Although the sites of genotypic variation between JEV-SA-14-14-2 and JEV-SA-14 were not coincident with hJEV-75 epitope residues, there are several residues in close proximity. For hJEV-75, the M/K279 genotypic variation is within 5 Å of epitope residue 49 or within 10 Å of epitope residues 273 and 275. Similarly, the K/E138 site of genotypic variation is within 10 Å of epitope residue 49, and the H/Q264 site of genotypic variation is also within 10 Å of the epitope residue 262. As an alternative explanation, differences in strain and genotype residues allosterically could affect the display of hJEV-75 epitopes. This idea has been described as a basis for differential neutralization of flavivirus genotypes by other antibodies (Austin et al., 2012 and Goo et al., 2017). Clearly, further studies with higher resolution epitope mapping of hJEV-75 (e.g. atomic resolution structures of the Fab-E complexes) may resolve this question of differential neutralization of JEV strains. Overall, these results have potential implications for assessing the breadth of the protective efficacy of existing and new JEV vaccines. It may be critical to assess whether antibody responses against the vaccine strain of a given JEV efficiently neutralize infection of heterologous genotypes, which may emerge.

Antibody hJEV-69 exhibited a loss of binding a result of alanine substitutions in E-DIII-LR, but charge substitutions in this region (S331K and S364K) did not affect hJEV-69 binding, suggesting a somewhat unique epitope. Consistent with this observation, FFWO studies of hJEV-69 indicated that although it inhibited at a post-attachment stage, it did not efficiently block pH-dependent fusion. Although further studies are required, the neutralizing human mAbs could block at a post-entry step before fusion. Alternatively, the FFWO, which is a measure of viral fusion at the plasma membrane, may not fully recapitulate the events occurring in the late endosome.

Protection studies were performed in vivo with human mAbs and JEV strains corresponding to the two most commonly circulating genotypes (I and III). To the inventor's knowledge, the protective effect of JEV mAbs against genotype I strains in vivo has not been studied previously. hJEV-75 completely protected against lethal JEV-Nakayama (GIII) infection when administered as prophylaxis. A single post-exposure dose of hJEV-75 provided high levels of protection against GI or GIII strains. Although prior studies have reported in vivo efficacy of murine and humanized E-DIII mAbs against JEV (Kimura-Kuroda and Yasui, 1988, Goncalvez et al., 2008 and Zhang et al., 1989), these challenge studies were performed with single, homologous JEV genotypes, and protection was limited to prophylaxis with the exception of a single study (Zhang et al., 1989). The post-exposure observed here is similar to that seen previously for other E-DIII-LR mAbs, including E16 and WNV (Stiasny et al., 2007) and E106 and DENV-1 (Shrestha et al., 2010). One caveat of this study is that administration of anti-JEV antibody at day 5 preceded the development of central nervous system symptoms (e.g., seizures, tremors, paralysis, or lethargy). More detailed window of treatment analysis is needed to determine which mAbs retain protective efficacy after the development of disease onset.

In summary, human anti-JEV mAbs that block infection at a post-attachment stage were identified. Overall, the combination of in vitro mAb neutralization analyses with mechanism of action, epitope mapping, and in vivo activity provides insight into developing and refining vaccine and therapeutic countermeasures against emerging JEV strains and genotypes.

TABLE 1

NUCLEOTIDE SEQUENCES FOR ANTIBODY VARIABLE REGIONS

| Clone | Variable Sequence Region | SEQ ID NO: |
|---|---|---|
| hJEV-11 Heavy | gaagttcagctggtcgagagtggtggaggattagttcagcctggaggatctcttagactgtcttgtgctgctagcg gcttcacctttccagctacgccatgtcttgggtgagacaagctccaggaaaaggacttgaatgggtgagcgtttc tggatctgccggagctaccacctattatgccgatagcgtgaagggcagatttaccatcagcagggacaacagca agaacaccctgtacctgcagatgaacagcctgagagccgaggatacagctgtgtactactgtgccaaggatgag tgggattacgactacatttggggcagctaccggtattggggacagggaacactggtgacagtgtctagc | 1 |
| hJEV-11 Light | gacatccagatgacacagagcccttctagcctttctgcctctgtgggagatagagtgaccatcacctgcagaaca agccagtctatcggcagatacctgaactggtaccagcagaaaccaggcaaagcccctaagctgctgatctttgct gcctcttctctgcagtctggagttcctagcagattttccggaagcggatctggcaccgactttacactgaccatca gctctctgcagctggaggattttgccacatactactgccagcagacctacatcaccctgatgtacacctttggcca gggcaccaaactggagatcaag | 2 |
| hJEV-69 Heavy | caggtgcagttacaggaatcaggtccaggactggtgaagccttctgaaacactgagcctgacatgtagcgtgag cggagattctgtgtctagcgccaaccactattggacatgggttagacagcctcctggaaaaggactggagtggat cggctacatgtaccacagcggaagcaccaattttcaccctagcctgaagtctagagtgaccatcagcgtggaca agagcaagaaccagttcagcctgaaactgaccagcgtgacagctgctgattctgccgtgtactactgtgccaga gttgatgctgtgatggagtactactacgagtctggaaccgctcctggcgccttcgatatttggggacagggaatta tggtgacagtgtcttct | 3 |
| hJEV-69 Light | gacatcgtgatgacccaaagccctgattctctggctgtgtctctgggagaaagagccaccatcaactgcaagag ctctcagtctgtgctgtacaggaacaacaacaagaactacctggcctggtaccagcacaagcctggccaaagcc ctaaactgctgatctattgggcctctacaagagaatctggcgtgcctgacagatttagcggcagcggctctggaa ccgattttacactgaccatctcttctttacaggccgaggatgtggctgtgtactactgccaccagtactacagcacc ccttacacctttggacaaggcacaaagctggagatcaag | 4 |
| hJev-75 Heavy | cagctgcaactccaagaatcaggtcctggactggtgaaacctagcgaaacactgagcctgacatgtaccgtgtc tggaggaagcatctctagcaccagctactattggggctggattagacagtctcctggaaaaggcctggagtgga tcggcagcatcttcaacaacggaagaaccttctacaaccctagcctgaagtctagggtgaccatcagcgtggac accagcaagaaccagtttagcctgaagctgtcttctgtgtctgctgccgatacagccatcttctactgcgccagac acctgatgtactctacaagcagcacagacgcctttgacatctggggacacggaacaatggtgacagtgagcagc | 5 |

TABLE 1-continued

NUCLEOTIDE SEQUENCES FOR ANTIBODY VARIABLE REGIONS

| Clone | Variable Sequence Region | SEQ ID NO: |
|---|---|---|
| hJev-75 Light | cagtctgccttaacccaaccagcttctgtgtctggatctcctggacagagcatcacaatgtcttgtaccggcacct ctagcgatgtgggcgattacaatctgctgagctggtaccagcaccatcctggaaaagctcctaagctgatgatct acgagggcagcaaaagaccttctggcgtgagcaacaggtttagcggcagcaaaagcggcaatacagcttctct gaccatttctggactgcaggccgaggatgaagccgattactactgttgcagctatgccggctcttctacatgggtt tttggaggcggcaccaaactgaccgttctg | 6 |
| hJEV-80 Heavy | caggtgcagttacaggaatcaggtccaggactggtgaagccttctgaaacactgagcctgacctgtacagtgtct ggaggaagcattagcagctactactggagctggatcagacagtctcctggcaaaggactggagtgtatcggcta catcttctacagcggcagcaccaactacaatcctagcctgaagagcagagtgaccatcagcgtggatgccagca aaaaccagttcagcctgaagctgagaagcgtgacagctgctgatacagccgtgtactattgcgccagagtgcttg gaagaatgagcttcgatcactggggacagggaacaccagtgacagtgtcttct | 7 |
| hJEV-80 Light | tcctatgtgctgactcagcccccctcggtgtcagtggcccaggacagacggccaggattacctgtggggaaac aacattggcagtaaaagtgtccactggtaccagcagaagtcagggcaggcccctgtgctggtcgtctataatgat agggaccggccctcagggatccctgagcgattctctggctccaactctgggaacacggcctccctgaccatcagc agggtcgaagccggggatgaggccgactattactgtcaggtgtgggataatggaagtgaccattatttcttcgga actgggaccaaggtcaccgtccta | 8 |

TABLE 2

PROTEIN SEQUENCES FOR ANTIBODY VARIABLE REGIONS

| Clone | Variable Sequence | SEQ ID NO: |
|---|---|---|
| hJEV-11 Heavy | EVQLVESGGGLVQPGGSLRLSCAASGFTFSSYAMSWVRQAPGKGLEW VSVSGSAGATTYYADSVKGRFTISRDNSKNTLYLQMNSLRAEDTAVYY CAKDEWDYDYIWGSYRYWGQGTLVTVSS | 9 |
| hJEV-11 Light | DIQMTQSPSSLSASVGDRVTITCRTSQSIGRYLNWYQQKPGKAPKLLIF AASSLQSGVPSRFSGSGSGTDFTLTISSLQLEDFATYYCQQTYITLMYTF GQGTKLEIK | 10 |
| hJEV-69 Heavy | QVQLQESGPGLVKPSETLSLTCSVSGDSVSSANHYWTWVRQPPGKGLE WIGYMYHSGSTNFHPSLKSRVTISVDKSKNQFSLKLTSVTAADSAVYY CARVDAVMEYYYESGTAPGAFDIWGQGIMVTVSS | 11 |
| hJEV-69 Light | DIVMTQSPDSLAVSLGERATINCKSSQSVLYRNNNKNYLAWYQHKPG QSPKLLIYWASTRESGVPDRFSGSGSGTDFTLTISSLQAEDVAVYYCHQ YYSTPYTFGQGTKLEIK | 12 |
| hJEV-75 Heavy | QLQLQESGPGLVKPSETLSLTCTVSGGSISSTSYYWGWIRQSPGKGLEW IGSIFNNGRTFYNPSLKSRVTISVDTSKNQFSLKLSSVSAADTAIFYCARH LMYSTSSTDAFDIWGHGTMVTVSS | 13 |
| hJEV-75 Light | QSALTQPASVSGSPGQSITMSCTGTSSDVGDYNLLSWYQHHPGKAPKL MIYEGSKRPSGVSNRFSGSKSGNTASLTISGLQAEDEADYYCCSYAGSS TWVFGGGTKLTVL | 14 |
| hJEV-80 Heavy | QVQLQESGPGLVKPSETLSLTCTVSGGSISSYYWSWIRQSPGKGLECIG YIFYSGSTNYNPSLKSRVTISVDASKNQFSLKLRSVTAADTAVYYCARV LGRMSFDHWGQGTPVTVSS | 15 |
| hJEV-80 Light | SYVLTQPPSVSVAPGQTARITCGGNNIGSKSVHWYQQKSGQAPVLVVY NDRDRPSGIPERFSGSNSGNTASLTISRVEAGDEADYYCQVWDNGSDH YFFGTGTKVTVL | 16 |

TABLE 3

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| hJEV-11 | GFTFSSYA 17 | SGSAGATT 18 | AKDEWDYDYIWGSYRY 19 |
| hJEV-69 | GDSVSSANHY 20 | MYHSGST 21 | ARVDAVMEYYYESGTAPGAFDI 22 |

TABLE 3 -continued

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| hJev-75 | GGSISSTSYY 23 | IFNNGRT 24 | ARHLMYSTSSTDAFDI 25 |
| hJEV-80 | GGSISSYY 26 | IFYSGST 27 | ARVLGRMSFDH 28 |

TABLE 4

CDR LIGHT CHAIN SEQUENCES

| Antibody | CDRH1 (SEQ ID NO:) | CDRH2 | CDRH3 (SEQ ID NO:) |
|---|---|---|---|
| hJEV-11 | QSIGRY 29 | AAS 30 | QQTYITLMYT 31 |
| hJEV-69 | QSVLYRNNNKNY 32 | WAS 33 | HQYYSTPYT 34 |
| hJev-75 | SSDVGDYNL 35 | EGS 36 | CSYAGSSTWV 37 |
| hJEV-80 | NIGSKS 38 | NDR 39 | QVWDNGSDHYF 40 |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

Abbondanzo et al., *Am. J. Pediatr. Hematol. Oncol.*, 12(4), 480-489, 1990.
Allred et al., *Arch. Surg.*, 125(1), 107-113, 1990.
Atherton et al., *Biol. of Reproduction*, 32, 155-171, 1985.
Austin et al., PLoS Pathog 8, 2012.
Barzon et al., *Euro Surveill.* 2016 Aug. 11; 21(32).
Beltramello et al., Cell Host Microbe 8, 2010.
Beltramello et al., *Cell Host Microbe* 8, 271-283, 2010.
Borah et al., J Clin Virol 52:45-49, 2011.
Brien et al., Propagation, Quantification, Detection, and Storage of West Nile Virus, p. 15D.3.1-15D.3.18, 2013.
Brown et al., *J. Immunol. Meth.*, 12; 130(1):111-121, 1990.
Burke et al., Southeast Asian J Trop Med Public Health 16:199-206, 1985.
Busby et al., Int J Mass Spectrom 259:130-139, 2007.
Campbell et al., Bull World Health Organ 89:766-74, 774A-774E, 2011.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.*, 74(2):425-433, 1977.
Chen et al., Am J Trop Med Hyg 47:61-69, 1992.
Chen et al., J Gen Virol 71:2915-2922, 1990.
Chen et al., J Microbiol Immunol Infect 42:296-302, 2009.
Chen et al., Proc Natl Acad Sci USA 6-11, 2016.
Cockburn et al., EMBO J 31:767-779, 2012.
Davidson and Doranz, Immunology 143:13-20, 2014.
De Jager et al., *Semin. Nucl. Med.* 23(2), 165-179, 1993.
Dholakia et al., *J. Biol. Chem.*, 264, 20638-20642, 1989.
Doolittle and Ben-Zeev, *Methods Mol. Biol.*, 109:215-237, 1999.
Duffy et al., N Engl J Med 2009; 360 (24) 2536-2543
Duffy et al., *N. Engl. J. Med.* 360, 2536-2543, 2009.
Edeling et al., Potent Dengue Virus Neutralization by a Therapeutic Antibody with Low Monovalent Affinity Requires Bivalent Engagement 10:e1004072, 2014.
Elder et al., Infections, infertility and assisted reproduction. Part II: Infections in reproductive medicine & Part III: Infections and the assisted reproductive laboratory. Cambridge UK: Cambridge University Press; 2005.
Gefter et al., *Somatic Cell Genet.*, 3:231-236, 1977.
Goncalvez et al., J Virol 82:7009-21, 2008.
Goo et al., PLoS Pathog 13, 2017.
Gornet et al., *Semin Reprod Med.* 2016 September; 34(5): 285-292. Epub 2016 Sep. 14.
Gulbis and Galand, *Hum. Pathol.* 24(12), 1271-1285, 1993.
Halfon et al., *PLoS ONE* 2010; 5 (5) e10569
Halstead and Solomon, Japanese Encephalitis, p. 317-333, 2010.
Hammon and Tigertt, Am J Hyg 50:51-6, 1949.
Health, Relev Epidemiol Hebd 90:69-87, 2015.
Hessell et al., Nature 449, 101-4, 2007.
Jarmer et al., J Virol 88:13845-13857, 2014.
Khatoon et al., *Ann. of Neurology*, 26, 210-219, 1989.
Kimura-Kuroda and Yasui, J Gen Virol 67:2663-2672, 1986.
Kimura-Kuroda and Yasui, J Immunol 141:3606-10, 1988.
Kimura-Kuroda and Yasui, J Virol 45:124-132, 1983.
King et al., *J. Biol. Chem.*, 269, 10210-10218, 1989.
Kohler and Milstein, *Eur. J. Immunol.*, 6, 511-519, 1976.
Kohler and Milstein, *Nature*, 256, 495-497, 1975.
Kyte and Doolittle, *J. Mol. Biol.*, 157(1):105-132, 1982.
Liang and Huanyu, Ther Clin Risk Manag 11:435, 2015.
Liao and Kielian, J Cell Biol 171:111-120, 2005.
Lin et al., J Virol 77:2600-6, 2003.
Luca et al., J Virol 86:2337-2346, 2012.
Ma et al., Am J Trop Med Hyg 69:151-4, 2003.
Mansuy et al., *Lancet Infect Dis.* 2016 October; 16(10): 1106-7.
Mason et al., J Gen Virol 70:2037-2049, 1989.
Mohammed et al., Infect Genet Evol 11:855-862, 2011.
Nakamura et al., In: *Enzyme Immunoassays: Heterogeneous and Homogeneous Systems*, Chapter 27, 1987.
Nybakken et al., J Virol 80:11467-11474, 2006.
Oliphant et al., J Virol 80:12149-12159, 2006.
O'Shannessy et al., *J. Immun. Meth.*, 99, 153-161, 1987.
Pal et al., PLoS Pathog 9:e1003312, 2013.
Persic et al., *Gene* 187:1, 1997
Pierson et al., Expert Rev Mol Med 10:e12, 2008.
Plotkin, Clin Vaccine Immunol, 2010.
Potter and Haley, *Meth. Enzymol.*, 91, 613-633, 1983.

Purpura et al., Lancet Infect Dis. 2016 October; 16(10): 1107-8. Epub 2016 Sep. 19.
Remington's Pharmaceutical Sciences, 15th Ed., 3:624-652, 1990.
Rey et al., Nature, 1995.
Robbiani et al., Cell 169:597-609.e11, 2017.
Roehrig et al., Virology 177:668-675, 1990.
Schuh et al., PLoS Negl Trop Dis 7, 2013.
Shimoda et al., Journal of Veterinary Medicine, 2013.
Shrestha et al., PLoS Pathog 6:e1000823, 2010.
Smith et al., MBio 4:e00873-13-e00873-13, 2013.
Solomon et al., Lancet 351:1094-7, 1998.
Solomon, J Neurol Neurosurg Psychiatry 68:405-415, 2000.
Stiasny et al., J Virol 81:11526-11531, 2007.
Studier, Protein Expr Purif 41:207-34, 2005.
Sukupolvi-Petty et al., J Virol 81:12816-26, 2007.
Takhampunya et al. Virol J 8:449, 2011.
Tang et al., *J. Biol. Chem.*, 271:28324-28330, 1996.
Thompson et al., PLoS Pathog 5:e1000453, 2009.
Throsby et al., J Virol 80:6982-92, 2006.
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
Uchil and Satchidanandam, Am J Trop Med Hyg 65:242-251, 2001.
Vaughn et al., Epidemiol Rev 14:197-221, 1992.
Vratskikh et al., PLoS Pathog 9, 2013.
Wahala et al., PLoS Pathog 6:1-10, 2010.
Wawrzynczak & Thorpe, In: *Immunoconjugates, Antibody Conjugates In Radioimaging And Therapy Of Cancer*, Vogel (Ed.), NY, Oxford University Press, 28, 1987.
WHO|Japanese encephalitis. WHO, 2017.
Xu et al., Proteomics 9:1548-1555, 2009.
Yan et al., Biochemistry 54:5322-5328, 2015.
Zhang et al., J Med Virol 29:133-138, 1989.
Zhao et al., Cell 166:1016-1027, 2016.

What is claimed is:

1. A method of detecting a Japanese Encephalitis virus infection in a subject comprising:
   (a) contacting a sample from said subject with an antibody or antigen-binding fragment thereof having heavy and light chain CDR1-3 sequences comprising SEQ ID NOS: 17-19 and 29-31, SEQ ID NOS: 26-28 and 38-40, SEQ ID NOS: 20-22 and 32-34 or SEQ ID NOS: 23-25 and 35-37, respectively; and (b) detecting Japanese Encephalitis virus in said sample by binding of said antibody or antibody fragment to a Japanese Encephalitis virus antigen in said sample.

2. A method of treating a subject infected with Japanese Encephalitis virus comprising delivering to said subject an effective amount an antibody or antigen-binding fragment thereof having heavy and light chain CDR1-3 sequences comprising SEQ ID NOS: 20-22 and 32-34 or SEQ ID NOS: 23-25 and 35-37, respectively.

3. The method of claim 2, the antibody or antigen-binding fragment thereof is encoded by light and heavy chain variable sequences comprised in SEQ ID NOS: 4 and 3 or SEQ ID NOS: 6 and 5, respectively.

4. The method of claim 2, the antibody or antigen-binding fragment thereof is encoded by light and heavy chain variable sequences having 95% identity in SEQ ID NOS: 4 and 3 or SEQ ID NOS: 6 and 5, respectively.

5. The method of claim 2, wherein said antibody or antigen-binding fragment thereof is encoded by light and heavy chain variable sequences having 70%, 80%, or 90% identity to comprised in SEQ ID NOS: 4 and 3 or SEQ ID NOS: 6 and 5, respectively.

6. The method of claim 2, wherein said antibody or antigen-binding fragment thereof comprises light and heavy chain variable sequences comprised in SEQ ID NOS: 12 and 11 or SEQ ID NOS: 14 and 13, respectively.

7. The method of claim 2, wherein said antibody or antigen-binding fragment thereof comprises light and heavy chain variable sequences having 70%, 80% or 90% identity to SEQ ID NOS: 12 and 11 or SEQ ID NOS: 14 and 13 respectively.

8. The method of claim 2, wherein said antibody or antigen-binding fragment thereof comprises light and heavy chain variable sequences having 95% identity to SEQ ID NOS: 12 and 11 or SEQ ID NOS: 14 and 13 respectively.

9. The method of claim 2, wherein the antigen-binding fragment thereof is a recombinant scFv (single chain fragment variable) antibody, Fab fragment, $F(ab')_2$ fragment, or Fv fragment.

10. The method of claim 2, wherein said antibody is an IgG, a recombinant IgG antibody or antigen-binding fragment thereof comprising an Fc portion mutated to alter FcR interactions, a glycan modified antibody with altered FcR interactions, a genetically modified glycosylating pattern, or an antibody or antigen-binding fragment thereof comprising an Fc portion mutated to enhance FcRn interactions to increase the in vivo half-life and the in vivo protective effect.

11. The method of claim 2, wherein said antibody is a chimeric antibody or a bispecific antibody.

12. The method of claim 2, wherein said subject is a pregnant female, a sexually active female, or a female undergoing fertility treatments.

13. The method of claim 2, wherein delivering comprises antibody or antigen-binding fragment thereof administration, or genetic delivery with an RNA or DNA sequence or vector encoding the antibody or antigen-binding fragment thereof.

14. An isolated monoclonal antibody or antigen-binding fragment thereof, comprising heavy and light chain CDR sequences comprising SEQ ID NOS: 17-19 and 29-31, SEQ ID NOS: 26-28 and 38-40, SEQ ID NOS: 20-22 and 32-34 or SEQ ID NOS 23-25 and 35-37, respectively.

15. A hybridoma or engineered cell encoding an antibody or antigen-binding fragment thereof, comprising heavy and light chain CDR1-3 sequences comprising SEQ ID NOS: 17-19 and 29-31, SEQ ID NOS: 26-28 and 38-40, SEQ ID NOS: 20-22 and 32-34 or SEQ ID NOS: 23-25 and 35-37, respectively.

16. A vaccine formulation comprising one or more antibodies or antigen-binding fragments thereof, comprising heavy and light chain CDR1-3 sequences comprising SEQ ID NOS: 20-22 and 32-34 or SEQ ID NOS: 23-25 and 35-37, respectively.

17. A method of determining stability over time of an antigen comprising:
(a) contacting a sample comprising said antigen with a first antibody or antigen-binding fragment thereof having heavy and light chain CDR1-3 sequences comprising SEQ ID NOS: 17-19 and 29-31, SEQ ID NOS: 26-28 and 38-40, SEQ ID NOS: 20-22 and 32-34 or SEQ ID NOS: 23-25 and 35-37, respectively; and
(b) determining stability over time of said antigen by detectable binding of said antibody or antigen-binding fragment thereof to said antigen.

18. The method of claim 17, further comprising:
(c) contacting a sample comprising said antigen with an antibody or antigen-binding fragment thereof having having heavy and light chain CDR1-3 sequences comprising SEQ ID NOS: 17-19 and 29-31, SEQ ID NOS: 26-28 and 38-40, SEQ ID NOS: 20-22 and 32-34 or SEQ ID NOS: 23-25 and 35-37, respectively; and
(d) determining stability over time of said antigen by detectable binding of said antibody or antigen-binding fragment thereof to said antigen.

19. The method of claim 10, wherein Fc portion mutated to alter FcR interactions comprises a LALA, N297, or GASD/ALIE mutation, or a glycan modified antibody with altered FcR interactions comprises enzymatic or chemical addition or removal of glycans, or an Fc portion mutated to enhance FcRn interactions to increase the in vivo half-life and the in vivo protective effect comprises a YTE or LS mutation.

20. The method of claim 13, wherein genetic delivery with an RNA or DNA sequence or vector encoding the antibody or antigen-binding fragment thereof employs a VEE replicon.

* * * * *

SEQUENCE LISTING

<160> NUMBER OF SEQ ID NOS: 49

<210> SEQ ID NO 1
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 1

```
gaagttcagc tggtcgagag tggtggagga ttagttcagc ctggaggatc tcttagactg      60
tcttgtgctg ctagcggctt cacctttcc agctacgcca tgtcttgggt gagacaagct     120
ccaggaaaag gacttgaatg ggtgagcgtt tctggatctg ccggagctac cacctattat    180
gccgatagcg tgaagggcag atttaccatc agcagggaca acagcaagaa cacctgtac     240 ctgcagatga acagcctgag agccgaggat acagctgtgt actactgtgc caaggatgag    300
tgggattacg actacatttg gggcagctac cggtattggg gacagggaac actggtgaca    360
gtgtctagc                                                            369
```

<210> SEQ ID NO 2
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 2

```
gacatccaga tgacacagag cccttctagc ctttctgcct ctgtgggaga tagagtgacc      60
atcacctgca gaacaagcca gtctatcggc agatacctga actggtacca gcagaaacca    120
ggcaaagccc ctaagctgct gatctttgct gcctcttctc tgcagtctgg agttcctagc    180
agattttccg gaagcggatc tggcaccgac tttacactga ccatcagctc tctgcagctg    240
```

-continued

| | |
|---|---|
| gaggattttg ccacatacta ctgccagcag acctacatca ccctgatgta cacctttggc | 300 |
| cagggcacca aactggagat caag | 324 |

<210> SEQ ID NO 3
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 3

| | |
|---|---|
| caggtgcagt tacaggaatc aggtccagga ctggtgaagc cttctgaaac actgagcctg | 60 |
| acatgtagcg tgagcggaga ttctgtgtct agcgccaacc actattggac atgggttaga | 120 |
| cagcctcctg aaaaggact ggagtggatc ggctacatgt accacagcgg aagcaccaat | 180 |
| tttcacccta gcctgaagtc tagagtgacc atcagcgtgg acaagagcaa gaaccagttc | 240 |
| agcctgaaac tgaccagcgt gacagctgct gattctgccg tgtactactg tgccagagtt | 300 |
| gatgctgtga tggagtacta ctacgagtct ggaaccgctc ctggcgcctt cgatatttgg | 360 |
| ggacagggaa ttatggtgac agtgtcttct | 390 |

<210> SEQ ID NO 4
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 4

| | |
|---|---|
| gacatcgtga tgacccaaag ccctgattct ctggctgtgt ctctgggaga aagagccacc | 60 |
| atcaactgca gagctctca gtctgtgctg tacaggaaca caacaagaa ctacctggcc | 120 |
| tggtaccagc acaagcctgg ccaaagccct aaactgctga tctattgggc ctctacaaga | 180 |
| gaatctggcg tgcctgacag atttagcggc agcggtctg aaccgatttt acactgacc | 240 |
| atctcttctt tacaggccga ggatgtggct gtgtactact gccaccagta ctacagcacc | 300 |
| ccttacacct ttggacaagg cacaaagctg gagatcaag | 339 |

<210> SEQ ID NO 5
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 5

| | |
|---|---|
| cagctgcaac tccaagaatc aggtcctgga ctggtgaaac ctagcgaaac actgagcctg | 60 |
| acatgtaccg tgtctggagg aagcatctct agcaccagct actattgggg ctggattaga | 120 |
| cagtctcctg aaaaggcct ggagtggatc ggcagcatct caacaacgg aagaaccttc | 180 |
| tacaacccta gcctgaagtc tagggtgacc atcagcgtgg acaccagcaa gaaccagttt | 240 |
| agcctgaagc tgtcttctgt gtctgctgcc gatacagcca tcttctactg cgccagacac | 300 |
| ctgatgtact ctacaagcag cacagacgcc tttgacatct ggggacacgg aacaatggtg | 360 |
| acagtgagca gc | 372 |

<210> SEQ ID NO 6
<211> LENGTH: 330
<212> TYPE: DNA

<210> SEQ ID NO 6
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 6

```
cagtctgcct taacccaacc agcttctgtg tctggatctc ctggacagag catcacaatg    60
tcttgtaccg gcacctctag cgatgtgggc gattacaatc tgctgagctg gtaccagcac   120
catcctggaa aagctcctaa gctgatgatc tacgagggca gcaaaagacc ttctggcgtg   180
agcaacaggt ttagcggcag caaaagcggc aatacagctt ctctgaccat ttctggactg   240
caggccgagg atgaagccga ttactactgt tgcagctatg ccggctcttc tacatgggtt   300
tttggaggcg gcaccaaact gaccgttctg                                    330
```

<210> SEQ ID NO 7
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 7

```
caggtgcagt tacaggaatc aggtccagga ctggtgaagc cttctgaaac actgagcctg    60
acctgtacag tgtctggagg aagcattagc agctactact ggagctggat cagacagtct   120
cctggcaaag gactggagtg tatcggctac atcttctaca gcggcagcac caactacaat   180
cctagcctga gagcagagt gaccatcagc gtggatgcca gcaaaaacca gttcagcctg   240
aagctgagaa gcgtgacagc tgctgataca gccgtgtact attgcgccag agtgcttgga   300
agaatgagct cgatcactg gggacaggga acaccagtga cagtgtcttc t             351
```

<210> SEQ ID NO 8
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 8

```
tcctatgtgc tgactcagcc cccctcggtg tcagtggccc aggacagac ggccaggatt     60
acctgtgggg gaaacaacat tggcagtaaa agtgtccact ggtaccagca gaagtcaggg   120
caggcccctg tgctggtcgt ctataatgat agggaccggc cctcagggat ccctgagcga   180
ttctctggct ccaactctgg gaacacggcc tccctgacca tcagcagggt cgaagccggg   240
gatgaggccg actattactg tcaggtgtgg gataatggaa gtgaccatta tttcttcgga   300
actgggacca aggtcaccgt ccta                                          324
```

<210> SEQ ID NO 9
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
                35                  40                  45
Ser Val Ser Gly Ser Ala Gly Ala Thr Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Glu Trp Asp Tyr Asp Tyr Ile Trp Gly Tyr Arg Tyr
                100                 105                 110
Trp Gly Gln Gly Thr Leu Val Thr Val Ser Ser
            115                 120

<210> SEQ ID NO 10
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 10

Asp Ile Gln Met Thr Gln Ser Pro Ser Ser Leu Ser Ala Ser Val Gly
  1               5                  10                  15
Asp Arg Val Thr Ile Thr Cys Arg Thr Ser Gln Ser Ile Gly Arg Tyr
                 20                  25                  30
Leu Asn Trp Tyr Gln Gln Lys Pro Gly Lys Ala Pro Lys Leu Leu Ile
             35                  40                  45
Phe Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Leu
 65                  70                  75                  80
Glu Asp Phe Ala Thr Tyr Tyr Cys Gln Gln Thr Tyr Ile Thr Leu Met
                 85                  90                  95
Tyr Thr Phe Gly Gln Gly Thr Lys Leu Glu Ile Lys
                100                 105

<210> SEQ ID NO 11
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 11

Gln Val Gln Leu Gln Glu Ser Gly Pro Gly Leu Val Lys Pro Ser Glu
  1               5                  10                  15
Thr Leu Ser Leu Thr Cys Ser Val Ser Gly Asp Ser Val Ser Ser Ala
                 20                  25                  30
Asn His Tyr Trp Thr Trp Val Arg Gln Pro Pro Gly Lys Gly Leu Glu
             35                  40                  45
Trp Ile Gly Tyr Met Tyr His Ser Gly Ser Thr Asn Phe His Pro Ser
 50                  55                  60
Leu Lys Ser Arg Val Thr Ile Ser Val Asp Lys Ser Lys Asn Gln Phe
 65                  70                  75                  80
Ser Leu Lys Leu Thr Ser Val Thr Ala Ala Asp Ser Ala Val Tyr Tyr
                 85                  90                  95
Cys Ala Arg Val Asp Ala Val Met Glu Tyr Tyr Tyr Glu Ser Gly Thr
                100                 105                 110
```

```
Ala Pro Gly Ala Phe Asp Ile Trp Gly Gln Gly Ile Met Val Thr Val
            115                 120                 125
Ser Ser
    130
```

<210> SEQ ID NO 12
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 12

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Arg
            20                  25                  30
Asn Asn Asn Lys Asn Tyr Leu Ala Trp Tyr Gln His Lys Pro Gly Gln
        35                  40                  45
Ser Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys His Gln
                85                  90                  95
Tyr Tyr Ser Thr Pro Tyr Thr Phe Gly Gln Gly Thr Lys Leu Glu Ile
            100                 105                 110
Lys
```

<210> SEQ ID NO 13
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 13

```
Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Thr
            20                  25                  30
Ser Tyr Tyr Trp Gly Trp Ile Arg Gln Ser Pro Gly Lys Gly Leu Glu
        35                  40                  45
Trp Ile Gly Ser Ile Phe Asn Asn Gly Arg Thr Phe Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Ser Ala Ala Asp Thr Ala Ile Phe Tyr
                85                  90                  95
Cys Ala Arg His Leu Met Tyr Ser Thr Ser Ser Thr Asp Ala Phe Asp
            100                 105                 110
Ile Trp Gly His Gly Thr Met Val Thr Val Ser Ser
            115                 120
```

<210> SEQ ID NO 14
<211> LENGTH: 110
<212> TYPE: PRT
<213> ORGANISM: Artificial sequence
<220> FEATURE:

<223> OTHER INFORMATION: Synthetic polypeptide

<400> SEQUENCE: 14

Gln Ser Ala Leu Thr Gln Pro Ala Ser Val Ser Gly Ser Pro Gly Gln
1               5                   10                  15

Ser Ile Thr Met Ser Cys Thr Gly Thr Ser Ser Asp Val Gly Asp Tyr
            20                  25                  30

Asn Leu Leu Ser Trp Tyr Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Trp Val Phe Gly Gly Gly Thr Lys Leu Thr Val Leu
            100                 105                 110

<210> SEQ ID NO 15
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Ser Pro Gly Lys Gly Leu Glu Cys Ile
        35                  40                  45

Gly Tyr Ile Phe Tyr Ser Gly Ser Thr Asn Tyr Asn Pro Ser Leu Lys
    50                  55                  60

Ser Arg Val Thr Ile Ser Val Asp Ala Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Val Leu Gly Arg Met Ser Phe Asp His Trp Gly Gln Gly Thr Pro
            100                 105                 110

Val Thr Val Ser Ser
            115

<210> SEQ ID NO 16
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 16

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Ser Gly Gln Ala Pro Val Leu Val Val Tyr
        35                  40                  45

Asn Asp Arg Asp Arg Pro Ser Gly Ile Pro Glu Arg Phe Ser Gly Ser

```
                50                  55                  60
Asn Ser Gly Asn Thr Ala Ser Leu Thr Ile Ser Arg Val Glu Ala Gly
 65                  70                  75                  80

Asp Glu Ala Asp Tyr Tyr Cys Gln Val Trp Asp Asn Gly Ser Asp His
                 85                  90                  95

Tyr Phe Phe Gly Thr Gly Thr Lys Val Thr Val Leu
                100                 105

<210> SEQ ID NO 17
<211> LENGTH: 8
<212> TYPE: PRT
<213> ORGANISM: Artificial sequence
<220> FEATURE:
<223> OTHER INFORMATION: Synthetic peptide

<400> SEQUENCE: 17

Gly Phe Thr Phe Ser Ser Tyr Ala
 1               5

<210> SEQ ID NO 18
<211> LENGTH: 8
<212> TYPE: PRT
<213> ORGANISM: Artificial sequence
<220> FEATURE:
<223> OTHER INFORMATION: Synthetic peptide

<400> SEQUENCE: 18

Ser Gly Ser Ala Gly Ala Thr Thr
 1               5

<210> SEQ ID NO 19
<211> LENGTH: 16
<212> TYPE: PRT
<213> ORGANISM: Artificial sequence
<220> FEATURE:
<223> OTHER INFORMATION: Synthetic peptide

<400> SEQUENCE: 19

Ala Lys Asp Glu Trp Asp Tyr Asp Tyr Ile Trp Gly Ser Tyr Arg Tyr
 1               5                  10                  15

<210> SEQ ID NO 20
<211> LENGTH: 10
<212> TYPE: PRT
<213> ORGANISM: Artificial sequence
<220> FEATURE:
<223> OTHER INFORMATION: Synthetic peptide

<400> SEQUENCE: 20

Gly Asp Ser Val Ser Ser Ala Asn His Tyr
 1               5                  10

<210> SEQ ID NO 21
<211> LENGTH: 7
<212> TYPE: PRT
<213> ORGANISM: Artificial sequence
<220> FEATURE:
<223> OTHER INFORMATION: Synthetic peptide

<400> SEQUENCE: 21

Met Tyr His Ser Gly Ser Thr
 1               5

<210> SEQ ID NO 22
<211> LENGTH: 22
```

```
<212> TYPE: PRT
<213> ORGANISM: Artificial sequence
<220> FEATURE:
<223> OTHER INFORMATION: Synthetic peptide

<400> SEQUENCE: 22

Ala Arg Val Asp Ala Val Met Glu Tyr Tyr Glu Ser Gly Thr Ala
1               5                   10                  15

Pro Gly Ala Phe Asp Ile
            20

<210> SEQ ID NO 23
<211> LENGTH: 10
<212> TYPE: PRT
<213> ORGANISM: Artificial sequence
<220> FEATURE:
<223> OTHER INFORMATION: Synthetic peptide

<400> SEQUENCE: 23

Gly Gly Ser Ile Ser Ser Thr Ser Tyr Tyr
1               5                   10

<210> SEQ ID NO 24
<211> LENGTH: 7
<212> TYPE: PRT
<213> ORGANISM: Artificial sequence
<220> FEATURE:
<223> OTHER INFORMATION: Synthetic peptide

<400> SEQUENCE: 24

Ile Phe Asn Asn Gly Arg Thr
1               5

<210> SEQ ID NO 25
<211> LENGTH: 16
<212> TYPE: PRT
<213> ORGANISM: Artificial sequence
<220> FEATURE:
<223> OTHER INFORMATION: Synthetic peptide

<400> SEQUENCE: 25

Ala Arg His Leu Met Tyr Ser Thr Ser Ser Thr Asp Ala Phe Asp Ile
1               5                   10                  15

<210> SEQ ID NO 26
<211> LENGTH: 8
<212> TYPE: PRT
<213> ORGANISM: Artificial sequence
<220> FEATURE:
<223> OTHER INFORMATION: Synthetic peptide

<400> SEQUENCE: 26

Gly Gly Ser Ile Ser Ser Tyr Tyr
1               5

<210> SEQ ID NO 27
<211> LENGTH: 7
<212> TYPE: PRT
<213> ORGANISM: Artificial sequence
<220> FEATURE:
<223> OTHER INFORMATION: Synthetic peptide

<400> SEQUENCE: 27

Ile Phe Tyr Ser Gly Ser Thr
1               5
```

<210> SEQ ID NO 28
<211> LENGTH: 11
<212> TYPE: PRT
<213> ORGANISM: Artificial sequence
<220> FEATURE:
<223> OTHER INFORMATION: Synthetic peptide

<400> SEQUENCE: 28

Ala Arg Val Leu Gly Arg Met Ser Phe Asp His
1               5                   10

<210> SEQ ID NO 29
<211> LENGTH: 6
<212> TYPE: PRT
<213> ORGANISM: Artificial sequence
<220> FEATURE:
<223> OTHER INFORMATION: Synthetic peptide

<400> SEQUENCE: 29

Gln Ser Ile Gly Arg Tyr
1               5

<210> SEQ ID NO 30
<211> LENGTH: 3
<212> TYPE: PRT
<213> ORGANISM: Artificial sequence
<220> FEATURE:
<223> OTHER INFORMATION: Synthetic peptide

<400> SEQUENCE: 30

Ala Ala Ser
1

<210> SEQ ID NO 31
<211> LENGTH: 10
<212> TYPE: PRT
<213> ORGANISM: Artificial sequence
<220> FEATURE:
<223> OTHER INFORMATION: Synthetic peptide

<400> SEQUENCE: 31

Gln Gln Thr Tyr Ile Thr Leu Met Tyr Thr
1               5                   10

<210> SEQ ID NO 32
<211> LENGTH: 12
<212> TYPE: PRT
<213> ORGANISM: Artificial sequence
<220> FEATURE:
<223> OTHER INFORMATION: Synthetic peptide

<400> SEQUENCE: 32

Gln Ser Val Leu Tyr Arg Asn Asn Asn Lys Asn Tyr
1               5                   10

<210> SEQ ID NO 33
<211> LENGTH: 3
<212> TYPE: PRT
<213> ORGANISM: Artificial sequence
<220> FEATURE:
<223> OTHER INFORMATION: Synthetic peptide

<400> SEQUENCE: 33

Trp Ala Ser
1

<210> SEQ ID NO 34

```
<211> LENGTH: 9
<212> TYPE: PRT
<213> ORGANISM: Artificial sequence
<220> FEATURE:
<223> OTHER INFORMATION: Synthetic peptide

<400> SEQUENCE: 34

His Gln Tyr Tyr Ser Thr Pro Tyr Thr
1               5

<210> SEQ ID NO 35
<211> LENGTH: 9
<212> TYPE: PRT
<213> ORGANISM: Artificial sequence
<220> FEATURE:
<223> OTHER INFORMATION: Synthetic peptide

<400> SEQUENCE: 35

Ser Ser Asp Val Gly Asp Tyr Asn Leu
1               5

<210> SEQ ID NO 36
<211> LENGTH: 3
<212> TYPE: PRT
<213> ORGANISM: Artificial sequence
<220> FEATURE:
<223> OTHER INFORMATION: Synthetic peptide

<400> SEQUENCE: 36

Glu Gly Ser
1

<210> SEQ ID NO 37
<211> LENGTH: 10
<212> TYPE: PRT
<213> ORGANISM: Artificial sequence
<220> FEATURE:
<223> OTHER INFORMATION: Synthetic peptide

<400> SEQUENCE: 37

Cys Ser Tyr Ala Gly Ser Ser Thr Trp Val
1               5                   10

<210> SEQ ID NO 38
<211> LENGTH: 6
<212> TYPE: PRT
<213> ORGANISM: Artificial sequence
<220> FEATURE:
<223> OTHER INFORMATION: Synthetic peptide

<400> SEQUENCE: 38

Asn Ile Gly Ser Lys Ser
1               5

<210> SEQ ID NO 39
<211> LENGTH: 3
<212> TYPE: PRT
<213> ORGANISM: Artificial sequence
<220> FEATURE:
<223> OTHER INFORMATION: Synthetic peptide

<400> SEQUENCE: 39

Asn Asp Arg
1

<210> SEQ ID NO 40
<211> LENGTH: 11
```

```
<212> TYPE: PRT
<213> ORGANISM: Artificial sequence
<220> FEATURE:
<223> OTHER INFORMATION: Synthetic peptide

<400> SEQUENCE: 40

Gln Val Trp Asp Asn Gly Ser Asp His Tyr Phe
1               5                   10

<210> SEQ ID NO 41
<211> LENGTH: 104
<212> TYPE: PRT
<213> ORGANISM: Artificial sequence
<220> FEATURE:
<223> OTHER INFORMATION: Synthetic polypeptide

<400> SEQUENCE: 41

Lys Gly Thr Thr Tyr Gly Met Cys Thr Glu Lys Phe Ser Phe Ala Lys
1               5                   10                  15

Asn Pro Val Asp Thr Gly His Gly Thr Val Val Ile Glu Leu Ser Tyr
                20                  25                  30

Ser Gly Ser Asp Gly Pro Cys Lys Ile Pro Ile Val Ser Val Ala Ser
            35                  40                  45

Leu Asn Asp Met Thr Pro Val Gly Arg Leu Val Thr Val Asn Pro Phe
        50                  55                  60

Val Ala Thr Ser Ser Ala Asn Ser Lys Val Leu Val Glu Met Glu Pro
65                  70                  75                  80

Pro Phe Gly Asp Ser Tyr Ile Val Val Gly Arg Gly Asp Lys Gln Ile
                85                  90                  95

Asn His His Trp His Lys Ala Gly
                100

<210> SEQ ID NO 42
<211> LENGTH: 104
<212> TYPE: PRT
<213> ORGANISM: Artificial sequence
<220> FEATURE:
<223> OTHER INFORMATION: Synthetic polypeptide

<400> SEQUENCE: 42

Lys Gly Val Ser Tyr Ser Leu Cys Thr Ala Ala Phe Thr Phe Thr Lys
1               5                   10                  15

Ile Pro Ala Glu Thr Leu His Gly Thr Val Thr Val Glu Val Gln Tyr
                20                  25                  30

Ala Gly Thr Asp Gly Pro Cys Lys Val Pro Ala Gln Met Ala Val Asp
            35                  40                  45

Met Gln Thr Leu Thr Pro Val Gly Arg Leu Ile Thr Ala Asn Pro Val
        50                  55                  60

Ile Thr Glu Ser Thr Glu Asn Ser Lys Met Met Leu Glu Leu Asp Pro
65                  70                  75                  80

Pro Phe Gly Asp Ser Tyr Ile Val Ile Gly Val Gly Glu Lys Lys Ile
                85                  90                  95

Thr His His Trp His Arg Ser Gly
                100

<210> SEQ ID NO 43
<211> LENGTH: 104
<212> TYPE: PRT
<213> ORGANISM: Artificial sequence
<220> FEATURE:
<223> OTHER INFORMATION: Synthetic polypeptide
```

```
<400> SEQUENCE: 43

Lys Phe Thr Thr Tyr Gly Val Cys Ser Lys Ala Phe Lys Phe Leu Gly
1               5                   10                  15

Thr Pro Ala Asp Thr Gly His Gly Thr Val Val Leu Glu Leu Gln Tyr
            20                  25                  30

Thr Gly Thr Asp Gly Pro Cys Lys Val Pro Ile Ser Ser Val Ala Ser
        35                  40                  45

Leu Asn Asp Leu Thr Pro Val Gly Arg Leu Val Thr Val Asn Pro Phe
    50                  55                  60

Val Ser Val Ala Thr Ala Asn Ala Lys Val Leu Ile Glu Leu Glu Pro
65                  70                  75                  80

Pro Phe Gly Asp Ser Tyr Ile Val Val Gly Arg Gly Glu Gln Gln Ile
                85                  90                  95

Asn His His Trp His Lys Ser Gly
            100

<210> SEQ ID NO 44
<211> LENGTH: 101
<212> TYPE: PRT
<213> ORGANISM: Artificial sequence
<220> FEATURE:
<223> OTHER INFORMATION: Synthetic polypeptide

<400> SEQUENCE: 44

Lys Gly Met Ser Tyr Val Met Cys Thr Gly Ser Phe Lys Leu Glu Lys
1               5                   10                  15

Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Thr Gln Asp Glu
        35                  40                  45

Lys Gly Ala Thr Gln Asn Gly Arg Leu Ile Thr Ala Asn Pro Ile Val
    50                  55                  60

Thr Asp Lys Glu Lys Pro Val Asn Ile Glu Ala Glu Pro Pro Phe Gly
65                  70                  75                  80

Glu Ser Tyr Ile Val Val Gly Ala Gly Glu Lys Ala Leu Lys Leu Ser
                85                  90                  95

Trp Phe Lys Lys Gly
            100

<210> SEQ ID NO 45
<211> LENGTH: 101
<212> TYPE: PRT
<213> ORGANISM: Artificial sequence
<220> FEATURE:
<223> OTHER INFORMATION: Synthetic polypeptide

<400> SEQUENCE: 45

Lys Gly Met Ser Tyr Val Met Cys Thr Gly Ser Phe Lys Leu Glu Lys
1               5                   10                  15

Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Ser Gln Asp Glu
        35                  40                  45

Lys Gly Val Thr Gln Asn Gly Arg Leu Ile Thr Ala Asn Pro Ile Val
    50                  55                  60

Thr Asp Lys Glu Lys Pro Val Asn Ile Glu Ala Glu Pro Pro Phe Gly
65                  70                  75                  80
```

```
Glu Ser Tyr Ile Val Val Gly Ala Gly Glu Lys Ala Leu Lys Leu Ser
                85                  90                  95

Trp Phe Lys Lys Gly
            100
```

<210> SEQ ID NO 46
<211> LENGTH: 101
<212> TYPE: PRT
<213> ORGANISM: Artificial sequence
<220> FEATURE:
<223> OTHER INFORMATION: Synthetic polypeptide

<400> SEQUENCE: 46

```
Lys Gly Met Ser Tyr Ser Met Cys Thr Gly Lys Phe Lys Val Val Lys
1               5                   10                  15

Glu Ile Ala Glu Thr Gln His Gly Thr Ile Val Ile Arg Val Gln Tyr
            20                  25                  30

Glu Gly Asp Gly Ser Pro Cys Lys Ile Pro Phe Glu Ile Met Asp Leu
        35                  40                  45

Glu Lys Arg His Val Leu Gly Arg Leu Ile Thr Val Asn Pro Ile Val
    50                  55                  60

Thr Glu Lys Asp Ser Pro Val Asn Ile Glu Ala Glu Pro Pro Phe Gly
65                  70                  75                  80

Asp Ser Tyr Ile Ile Gly Val Glu Pro Gly Gln Leu Lys Leu Asn
                85                  90                  95

Trp Phe Lys Lys Gly
            100
```

<210> SEQ ID NO 47
<211> LENGTH: 101
<212> TYPE: PRT
<213> ORGANISM: Artificial sequence
<220> FEATURE:
<223> OTHER INFORMATION: Synthetic polypeptide

<400> SEQUENCE: 47

```
Lys Gly Met Ser Tyr Ala Met Cys Leu Asn Thr Phe Val Leu Lys Lys
1               5                   10                  15

Glu Val Ser Glu Thr Gln His Gly Thr Ile Leu Ile Lys Val Glu Tyr
            20                  25                  30

Lys Gly Glu Asp Ala Pro Cys Lys Ile Pro Phe Ser Thr Glu Asp Gly
        35                  40                  45

Gln Gly Lys Ala His Asn Gly Arg Leu Ile Thr Ala Asn Pro Val Val
    50                  55                  60

Thr Lys Lys Glu Glu Pro Val Asn Ile Glu Ala Glu Pro Pro Phe Gly
65                  70                  75                  80

Glu Ser Asn Ile Val Ile Gly Ile Gly Asp Lys Ala Leu Lys Ile Asn
                85                  90                  95

Trp Tyr Arg Lys Gly
            100
```

<210> SEQ ID NO 48
<211> LENGTH: 101
<212> TYPE: PRT
<213> ORGANISM: Artificial sequence
<220> FEATURE:
<223> OTHER INFORMATION: Synthetic polypeptide

<400> SEQUENCE: 48

```
Lys Gly Met Ser Tyr Thr Met Cys Ser Gly Lys Phe Ser Ile Asp Lys
1               5                   10                  15

Glu Met Ala Glu Thr Gln His Gly Thr Thr Val Val Lys Val Lys Tyr
            20              25                  30

Glu Gly Ala Gly Ala Pro Cys Lys Val Pro Ile Glu Ile Arg Asp Val
        35              40              45

Asn Lys Glu Lys Val Val Gly Arg Ile Ile Ser Ser Thr Pro Phe Ala
    50              55              60

Glu Asn Thr Asn Ser Val Thr Asn Ile Glu Leu Glu Pro Pro Phe Gly
65              70              75                      80

Asp Ser Tyr Ile Val Ile Gly Val Gly Asp Ser Ala Leu Thr Leu His
            85              90                  95

Trp Phe Arg Lys Gly
            100

<210> SEQ ID NO 49
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(20)
<223> OTHER INFORMATION: phosphorothioate-modified oligodeoxynucleotide

<400> SEQUENCE: 49
tcgtcgtttt tcggtcgttt t                                           21
```